(12) United States Patent
Paolitto et al.

(10) Patent No.: US 8,007,515 B2
(45) Date of Patent: *Aug. 30, 2011

(54) SUTURE RETENTION DEVICE

(75) Inventors: Anthony Paolitto, St. Leonard (CA); Valerio Valentini, Montreal (CA); Raymond Cartier, Montreal (CA)

(73) Assignee: Coroneo, Inc., Montreal, Quebec (CA)

( * ) Notice: Subject to any disclaimer, the term of this patent is extended or adjusted under 35 U.S.C. 154(b) by 560 days.

This patent is subject to a terminal disclaimer.

(21) Appl. No.: 11/689,768

(22) Filed: Mar. 22, 2007

(65) Prior Publication Data
US 2007/0179511 A1    Aug. 2, 2007

Related U.S. Application Data

(63) Continuation of application No. 10/365,481, filed on Feb. 13, 2003, now abandoned, which is a continuation of application No. 09/762,437, filed as application No. PCT/CA99/00740 on Aug. 10, 1999, now Pat. No. 6,547,725.

(30) Foreign Application Priority Data

Aug. 10, 1998  (CA) ...................................... 2242295

(51) Int. Cl.
*A61B 1/32* (2006.01)
*A61B 17/10* (2006.01)
(52) U.S. Cl. ........ 606/232; 600/232; 600/233; 600/210; 606/139
(58) Field of Classification Search .................. 600/232, 600/210, 229, 231; 606/232, 139
See application file for complete search history.

(56) References Cited

U.S. PATENT DOCUMENTS

| | | | |
|---|---|---|---|
| 1,706,500 | A | 3/1929 | Smith |
| 3,129,706 | A | 4/1964 | Reynolds, Jr. |
| 3,625,220 | A | 12/1971 | Engelsher |
| 3,650,274 | A | 3/1972 | Edwards et al. |
| 3,730,129 | A | 5/1973 | Helms |
| 3,765,061 | A | 10/1973 | Nash |
| 3,831,608 | A | 8/1974 | Kletschka et al. |
| 3,934,592 | A | 1/1976 | Wolvek et al. |
| 3,965,890 | A | 6/1976 | Gauthier |
| 4,492,229 | A | 1/1985 | Grunwald |
| 4,627,421 | A | 12/1986 | Symbas et al. |
| 4,796,846 | A | 1/1989 | Meier et al. |
| 4,956,897 | A | 9/1990 | Speedie |
| 5,025,779 | A | 6/1991 | Bugge |

(Continued)

FOREIGN PATENT DOCUMENTS
EP      0791330 A2      8/1997
(Continued)

*Primary Examiner* — Vy Q Bui
(74) *Attorney, Agent, or Firm* — Wood, Herron & Evans, L.L.P.

(57) ABSTRACT

A tissue retractor for displacing body tissue during surgery includes a tissue piercing member such as a surgical needle, a wire-like filament such as a suture line affixed to the surgical needle, a fixed element such as an anchoring port being associated with a stable surgical platform such as a sternum retractor and a movable element such as an anchoring plug cooperating with anchoring port to engage a portion of suture line after the suture line is threaded through the body tissue with the surgical needle and after the suture wire is tensioned to effect a predetermined displacement of the body tissue. The predetermined displacement of body tissue is maintained by retention of the engaged portion of suture line by the fixed anchoring port and the movable anchoring plug.

18 Claims, 18 Drawing Sheets

U.S. PATENT DOCUMENTS

| | | | |
|---|---|---|---|
| 5,172,455 A | | 12/1992 | Johnson et al. |
| 5,356,412 A | * | 10/1994 | Golds et al. .................... 606/74 |
| 5,375,481 A | | 12/1994 | Cabrera et al. |
| 5,503,617 A | | 4/1996 | Jako |
| 5,852,853 A | * | 12/1998 | Pennoyer, Jr. ............... 24/134 P |
| 5,968,076 A | | 10/1999 | Granger et al. |
| 5,996,265 A | | 12/1999 | Coury |
| 6,010,531 A | | 1/2000 | Donlon et al. |
| 6,102,854 A | * | 8/2000 | Cartier et al. ................. 600/228 |
| 6,123,571 A | | 9/2000 | Craft, Jr. |
| 6,213,940 B1 | | 4/2001 | Sherts et al. |
| 6,231,506 B1 | | 5/2001 | Hu et al. |
| 6,283,912 B1 | | 9/2001 | Hu et al. |
| 6,331,157 B2 | | 12/2001 | Hancock |
| 6,331,158 B1 | | 12/2001 | Hu et al. |
| 6,652,454 B2 | | 11/2003 | Hu et al. |

FOREIGN PATENT DOCUMENTS

EP  0808606 A1  11/1997

\* cited by examiner

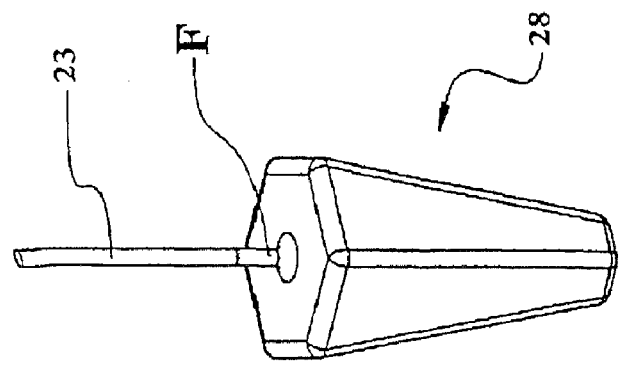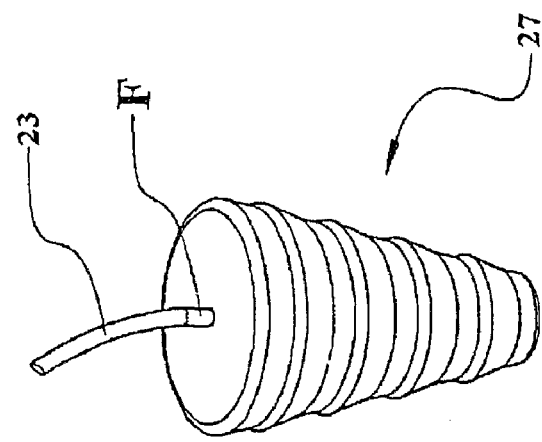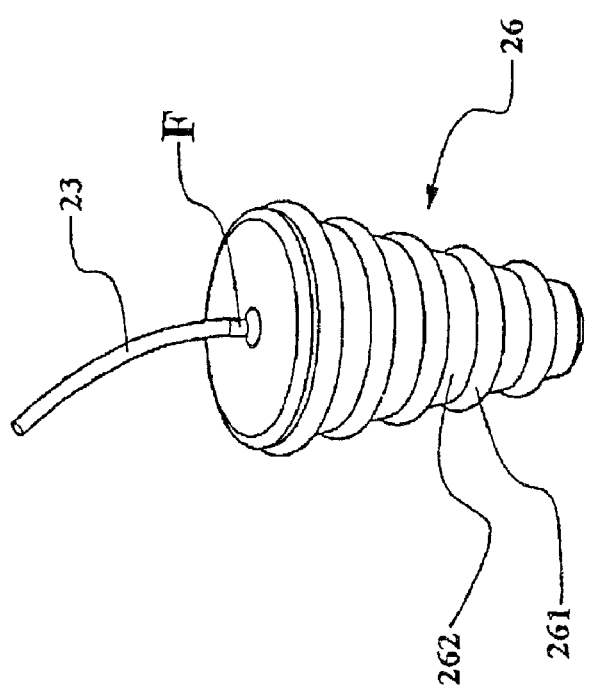
Figure 2C
Figure 2B
Figure 2A

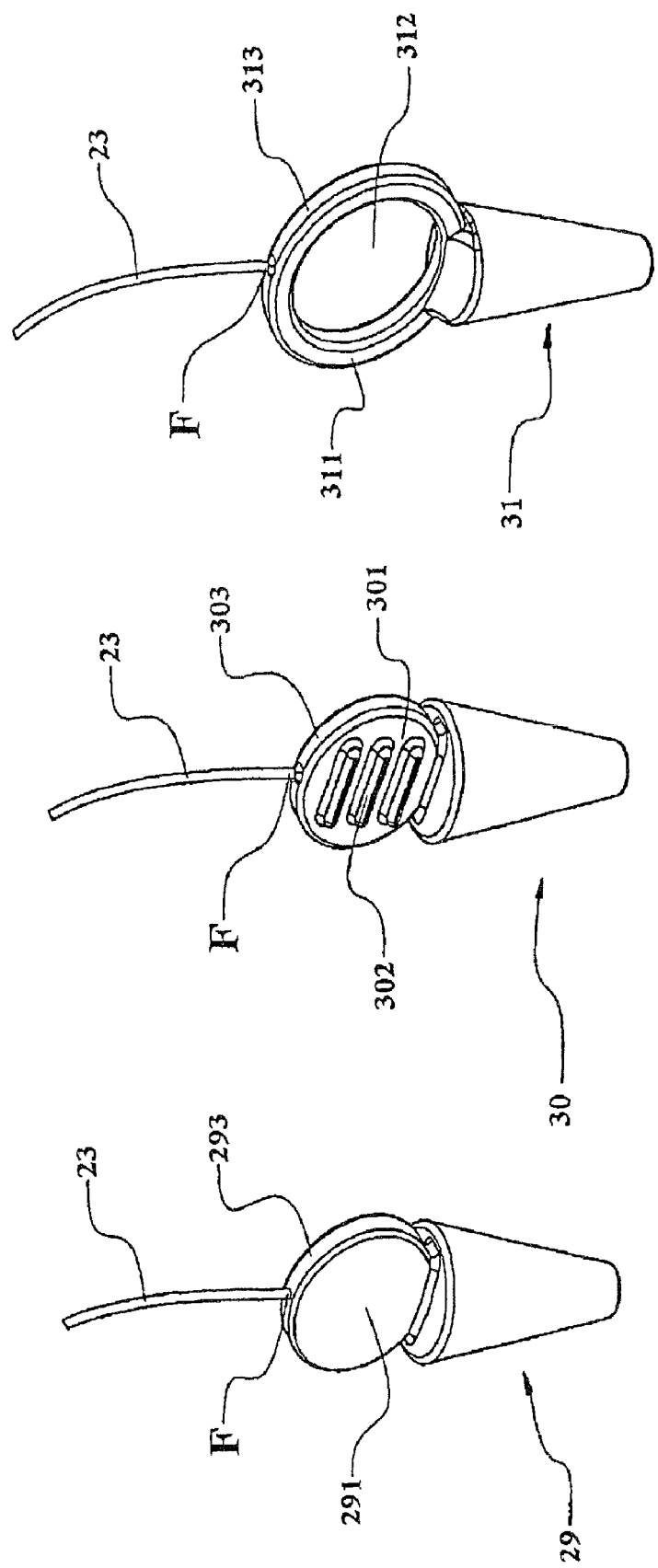

SUTURE RETENTION DEVICE

This application is a continuation application of prior U.S. patent application Ser. No. 10/365,481, filed on Feb. 13, 2003 (pending) which is a continuation of U.S. patent application Ser. No. 09/762,437, filed on Apr. 10, 2001 (now U.S. Pat. No. 6,547,725) which is a U.S. National Stage of International Application No. PCT/CA99/00740, filed on Aug. 10, 1999 (expired), which claims the priority of Canadian Patent Application No. 2242295, filed Aug. 10, 1998, the disclosures of which are incorporated by reference herein.

FIELD OF THE INVENTION

The present invention relates to the field of surgical apparatus and more specifically, to a suture and associated anchoring mechanism for applying tissue retraction during surgery.

BACKGROUND OF THE INVENTION

Generally, surgery requires an incision through a patient's skin, underlying muscle and tissue to expose the underlying body organ or anatomical tissue which is in need of the particular surgical intervention. In certain types of surgery such as cardiac surgery for instance, the patient's bone structure may also be incised and retracted. This is the case with a midline sternotomy incision which incises the patient's sternum and retracts the ribcage, or in situations where bone structure is spread apart without incision thereof as with an intercostal thoracotomy incision in which two adjacent patient ribs are spread apart in order to expose the underlying body organ, namely the patient's heart.

To obtain and maintain a surgical window or opening onto the underlying body organ or tissue in relation to which the surgical intervention will take place, abdominal or thoracic surgical retractors are used subsequent to the initial incision to spread the incised body tissue. Surgical retractors exist in many sizes and shapes and have been present since the dawn of surgery. Most known retractors have an elongate rack bar and two retracting arms, namely a fixed retracting arm and a movable retracting arm. Both arms typically extend in a direction normal to the rack bar. The movable arm can be displaced along the rack bar, and relative to the fixed arm, by using a crank to activate a pinion mechanism which engages teeth on the rack bar. Two blades are provided, usually disposed below the retractor arm and extending into the surgical incision, to interface with the patient's skin and tissue and to apply the retraction that creates the surgical window by relative movement and an ensuing spacing apart of the two retractor arms. The retractor blades may also engage with the patient's bone structure during surgery that requires access to tissue or organs contained within the patient's thorax. This is the case with coronary artery bypass graft (CABG) surgery, where the patient's skin and incised sternum are engaged with the blades of a surgical retractor known as a sternum or sternal retractor. The basic surgical approach and surgical retractor design for creating a surgical window onto the underlying tissue and organs requiring the surgical intervention, whereby the two or more spreader members or retractor arms are moved apart to retract engaged tissue, have remained relatively unchanged since the first introduction of retractors to surgery, regardless of the type, size and shape of the surgical retractor. The surgeon may at times place a sterile drape, cloth, or other type of packing between the patient's incised body tissue and the interfacing blades or other portion of the surgical retractor.

Once the surgical window is created, the surgeon often times will retract other internal body tissue which becomes accessible through the surgical window, with a flexible wire-like filament having a tissue-piercing member on one end of the wire-like filament, such as a suture line with integral needle on one end of the suture line. The suture line with the integral tissue piercing needle at one end will be referred to herein as the "traditional suture" or simply the "suture".

A standard technique for retraction of coronary tissue during cardiac surgery has been the use of sutures, including traction sutures and stay sutures. These sutures are well known in the field of cardiac surgery and are available in a variety of needle configurations, suture length and diameter thicknesses. The sutures are generally available in kit form in disposable sterilized packets containing a needle and a length of filament.

Internal body tissue may be retracted for a number of reasons during surgery, namely:

a) to improve access to the target body organ or target organ tissue requiring the surgical intervention; this may be accomplished by displacing or retracting surrounding internal body tissue that may obstruct, restrict or impede surgical access, as for instance when retracting fatty tissue;

b) to maintain access to the inside of an organ cavity or body vessel subsequent to an incision of the organ or vessel; this may be accomplished by retracting incised portions of organ tissue or vessel tissue, as for instance when retracting incised portions of the aorta to maintain access to the aortic valve;

c) to position or orient at least a portion of the body organ; this may be accomplished through retraction of surrounding tissue which is anatomically attached to the body organ or through retraction of the body organ directly.

Tissue retraction is typically achieved by piercing the body organ or body tissue with a needle at the end of a suture line, threading a length of suture line through the pierced body tissue, and pulling simultaneously on both resulting lengths of the suture line; that is, the length between the pierced tissue and the free end of the suture line, and the length between the pierced tissue and the needle-bearing end of the suture line. Retraction loads are imposed on the body tissue or body organ at the location where the needle pierces and penetrates through the tissue or the organ.

In most surgical procedures, retraction is maintained by securing the above mentioned two lengths of the suture line by accomplishing one of the following techniques:

a) tying the free end and needle-bearing end of the suture line to each other through another part of the patient's anatomy, preferably remote to the location of body tissue where the surgical intervention will take place;

b) simultaneously clamping these two lengths of suture line to other body tissue or to the sterile cloth or packing inserted between the surgical retractor and the patient's incised tissue creating the surgical window;

c) clamping these two lengths to the surgical retractor with a surgical clamp or tying the free end and the needle-bearing end of these two lengths to each other and to a portion of the surgical retractor;

d) clamping these two lengths with a surgical clamp and wedging the tip or at least a portion of the surgical clamp between the retractor and the patient's body or between the retractor and the sterile cloth or packing placed along the surgical incision and trapped between the retractor blades and patient's body.

The current methods described above of maintaining tissue retraction may, in some instances:

a) be time consuming, since securing of the retraction load through the manual tying of the suture line lengths is a multi-step threading and knotting procedure;

b) be cumbersome due to poor access during the manual tie down of the suture line lengths, especially in surgical interventions when the surgical window is small;

c) not be conducive to readjustment of the magnitude of the desired tensile retraction load on the organ or body tissue, or on the direction of said load relative to the organ or body tissue without having to untie and retie suture line lengths or without having to cut the existing suture line having the undesired retraction load and replacing it with a new suture that must again pierce the organ or body tissue and be secured by way of one of the methods listed above;

d) compromise the ergonomics of and the surgeon's access into the surgical window, especially when a surgical clamp is used to secure the two lengths of the suture line to the perimeter of the surgical window or to a portion of the surgical retractor used to create the surgical window, all the more when multiple suture lines need to be secured to achieve the desired organ or body tissue retraction;

e) hinder or restrict the readjustment of the surgical window opening through the opening or closing of the surgical retractor, if the lengths of the suture line are tied to the rack bar of the surgical retractor, or hinder the deployment or readjustment of peripheral surgical devices that are mounted or need to be mounted on the spreader arms of the retractor.

Generally, adjustment of the desired tensile retraction by cutting an existing suture line and repiercing a new suture line is not desirable. First, the process of placing a suture requires considerable manual dexterity, at times requiring the help of an assistant. The process is therefore tedious and time consuming. Second, a repiercing of the internal body tissue or body organ with a subsequent suture tends to increase the likelihood of inducing tissue trauma or tissue tearing which may have to be surgically repaired.

More recently with the advent of minimally invasive surgical techniques, laparoscopic approaches have been developed. Consequently, the surgical access windows into the patient's abdomen or thorax have become smaller. However, internal tissue retraction through a suture (suture line with a tissue piercing needle attached to at least one end) remains a requirement in certain types of surgical interventions. This tissue retraction with suture tends to generally be more difficult due to the smaller access through a laparoscopic entry relative to the larger surgical access window obtained through the traditional retracted incision entry.

Although the principles of this invention may be applied to many types of surgeries requiring tissue retraction by the application and maintenance of a tensile load on a suture, the examples will focus on cardiac surgery; and more specifically, on CABG surgery performed on the beating heart. In addition, although the examples will refer to retraction of internal body tissue, the concepts and principles may also be extended to external body tissue, as those skilled in this art will appreciate.

CABG surgery has been traditionally performed with the support of the cardiopulmonary machine, whereby the patient's blood is oxygenated outside the body through extracorporeal circulation (ECC). This allows the surgeon to manipulate and operate on a perfectly still heart. During traditional CABG surgery, the surgeon or assistant can manually position and orient the arrested heart for best access to the target artery requiring the bypass graft.

Recently, in an aim to render CABG surgery less invasive to the patient, beating heart CABG surgery is being developed whereby ECC, one of the most invasive aspects of cardiac surgery, is eliminated and coronary artery revascularization is performed directly on the beating heart. One of the challenges in performing beating heart CABG surgery lies in positioning and orienting the beating heart in order to obtain access to the inferior and posterior artery beds, while tending to minimize physiologically undesirable effects such as hemodynamic instability, arrhythmia, or a precipitous drop in arterial pressure, that may occur as a result of such manipulations. In traditional CABG surgery the heart is arrested and therefore heart manipulations are well tolerated.

During CABG surgery or beating heart CABG surgery, the pericardium, namely the membranous sac in which the heart and the commencement of the major blood vessels connecting with the heart are contained, is generally incised and unraveled to expose at least a portion of the heart surface which is to receive the bypass graft. The pericardium tissue, unlike the heart, is not beating and can be separated from the heart surface except in some locations where it is anatomically attached to the heart. Thus, it is surgically possible to position or orient the heart by manipulating the pericardium tissue to which it is attached. In beating heart CABG surgery, it may be desirable to position and orient the beating heart through retraction of the pericardium tissue to obtain access to the inferior and posterior coronary artery beds. The likelihood of inducing trauma to the beating heart tends to be reduced, and the physiologically undesirable effects mentioned above tend to be reduced, since direct contact with the beating heart is avoided and the manipulations are achieved through retraction of the pericardium tissue which, although incised remains anatomically attached to the beating heart in certain locations.

Based on the foregoing, it would therefore be advantageous to provide a suture with an integral anchoring member that may be inserted into an anchoring port of a stable platform (such as a surgical retractor) to tend to achieve and maintain the desired tissue retraction load on the organ or body tissue of the patient in a relatively quicker and more convenient fashion than some of the prior art methods described above.

Alternatively, based on the foregoing, it would also be advantageous to provide a surgical retractor configured with an integral suture anchoring mechanism or add-on suture anchoring mechanism capable of engaging a traditional suture (namely, as explained above, a suture comprised of a suture line with tissue piercing needle attached to at least one end) to tend to achieve and maintain the desired tissue retraction load on the organ or body tissue of the patient in a relatively quicker and more convenient fashion than some of the current methods described above.

Thus it is one of the objects of the present invention to aim to reduce deployment times associated to the placement of tissue retraction sutures and to facilitate the securement thereof during surgery.

It is another object of the present invention to provide a tissue retractor comprising a suture line allowing the retraction of body tissue or body organs during the surgical intervention that aims to eliminate the operation of manually tying suture line lengths to one another through a multi-step threading and knotting procedure in order to achieve the said retraction.

It is another object of the present invention to provide a tissue retractor comprising a suture line allowing the retraction of internal body tissue or body organs during the surgical intervention which permits the readjustment of the retraction force applied by said suture line to the internal body tissue, either in magnitude or in direction, without requiring the severing or disposal of said suture line and without the removal of said suture line from internal body tissue.

These and other objects of the present invention will become apparent from the description of the present invention and its preferred embodiments which follows.

SUMMARY OF THE INVENTION

According to one broad aspect of the present invention, there is provided a tissue retractor for displacing body tissue during surgery, the tissue retractor comprising a surgical tissue piercing member; a suture line affixed to the surgical tissue piercing member; a fixed element, the fixed element being associated with a stable surgical platform; a movable element, the movable element cooperating with the fixed element to engage a portion of the suture line after the suture line is threaded through the body tissue with the surgical tissue piercing member and after the threaded suture line is tensioned to effect a predetermined displacement of said body tissue; and wherein said predetermined displacement of said body tissue is maintained by retention of the engaged portion of the suture line by the movable element and the fixed element.

In some surgical interventions, the foregoing features contribute to attempt to position and orient the beating heart through retraction of the incised pericardium tissue during beating heart CABG, while tending to minimize the likelihood of inducing physiologically adverse effects such as hemodynamic instability, arrhythmia, or a precipitous drop in arterial pressure.

BRIEF DESCRIPTION OF THE DRAWINGS

For better understanding of the present invention and to show more clearly how it may be carried into effect, reference will now be made by way of illustration and not of limitation to the accompanying drawings, which show an apparatus according to preferred embodiments of the present invention, and in which:

FIGS. 2A to 2C illustrate several variants of anchoring members of the anchoring mechanism with reference to the first embodiment of FIGS. 1A to 1D;

FIGS. 3A to 3C illustrate several variants of an anchoring member of the anchoring mechanism of the first embodiment of FIGS. 1A to 1D comprising an anchoring member handle;

DETAILED DESCRIPTION OF THE ILLUSTRATIVE EMBODIMENTS

The features and principles of this invention can be applied, in whole or in part, to many types of surgical procedures including those which rely on surgical retractors to create and maintain a surgical window into the patient's incised skin for access into the patient's abdomen or thorax, and those which rely on laparoscopic entry ports into the patient's skin to gain such access. The description of the preferred embodiments will be illustrated with respect to sternum retractors used in cardiac surgery, for instance those used to perform traditional CABG surgery with ECC, beating heart CABG without ECC, or valve surgery through a midline sternotomy incision. However, some of the features and principles may also apply to other types of retractors, such as abdominal retractors and thoracic retractors used in other types of surgical procedures. Some of the features and principles may even apply to other substantially stable surgical platforms which can be configured with an anchoring port or anchoring mechanism as described and illustrated in the embodiments herein. Such surgical platforms would include: a surgical table, a surgical bridge or truss member attached to a surgical table and spanning the patient or set adjacent the patient; a surgical attachment for fixturing an instrument used in laparoscopic surgery to a surgical table, surgical bridge or truss, or a surgical instrument as may be used in laparoscopic surgery, or other like platforms.

In part, the embodiments of this invention may advantageously be applied, if desired, to the retractor described in copending Canadian patent application Serial No. 2,216,893 filed on Sep. 30, 1997 in the names of Cartier and Paolitto and entitled "Sternum Retractor for Performing Bypass Surgery on the Beating Heart", and in copending Canadian patent application Serial No. 2,232,795 filed on May 22, 1998 in the names of Paolitto et al. and entitled "Manipulation and Adjustment of Surgical Instruments", the contents of each of which are incorporated herein by reference. These existing applications have been assigned to CoroNéo Inc., the assignee of the present application.

Figure 1A:
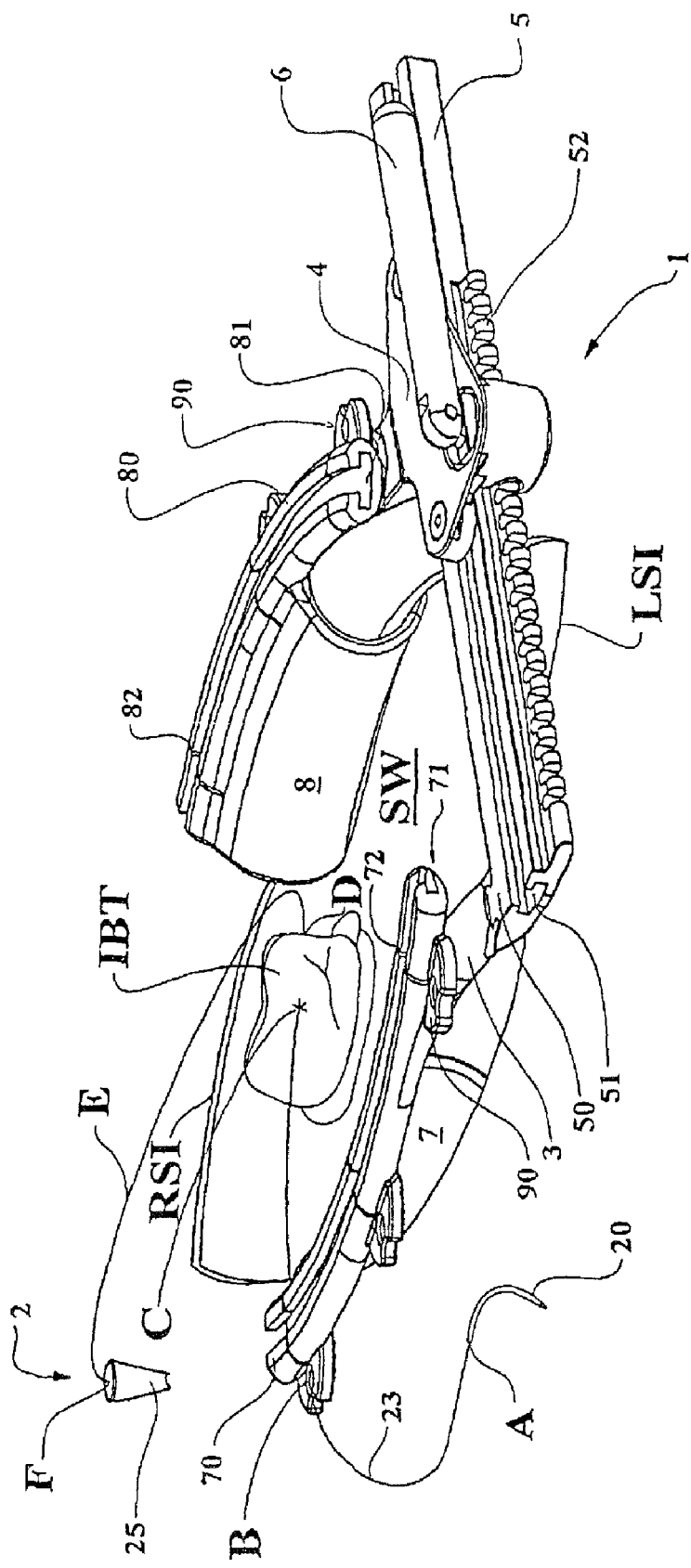
FIG. 1A is a perspective view illustrating a tissue retractor comprising a suture and associated anchoring mechanism according to a first embodiment of the present invention.

By way of a general overview and with reference to FIG. 1A, a surgical apparatus with which the invention may be used is comprised of two main components, a tissue retractor 2 and a sternum retractor 1. The sternum retractor 1 is provided with a plurality of anchoring ports 90 to receive at least one said tissue retractor 2 in at least one said anchoring port 90, in order to effectuate the desired tissue retraction of internal body tissue (labeled IBT). The tissue retractor 2 is illustrated after having pierced internal body tissue IBT, prior to its intended engagement with the sternum retractor 1 and more specifically with one of the anchoring ports 90 thereof. The sternum retractor 1 is illustrated in its deployed state, thereby creating and maintaining the surgical window (labeled SW) that provides the surgeon with access to the patient's internal coronary organs, which include the heart, the pericardium tissue, the aorta and vena cava, the coronary arteries and veins, the pleurae, the thymus, and other anatomical features, all of which are collectively and schematically depicted as internal body tissue IBT.

The sternum retractor 1 includes four major parts: (i) an elongated rack bar 5, (ii) a first retractor spreader arm 3 being preferably fixed to the rack bar 5, (iii) a second retractor spreader arm 4 being preferably movable with respect to the rack bar 5, and (iv) an actuator 6 for effecting movement of the retractor spreader arm 4 relative to retractor spreader arm 3.

Retractor spreader arms 3 and 4 extend in a direction substantially transversely with regard to the rack bar 5, generally in the same direction therefrom and in a parallel orientation with respect to one another. The movable arm 4 can be displaced along the rack bar 5, and relative to the other arm 3, preferably through the rotation of the actuator 6 activated by the surgeon. The actuator 6 is operatively connected to the rack bar 5 and to the other spreader arm 4, and is translatable along the length of the rack bar 5. This is preferably achieved by the engagement of a pinion mechanism (not shown) of actuator 6 with the rack teeth 52 on rack bar 5. Two retractor blades 7 (not wholly visible in FIG. 1A) and 8 are respectively provided with the retractor spreader arms 3 and 4, preferably disposed below the rack bar 5 when the sternum retractor 1 is deployed on a patient. The retractor blades 7 and 8 engage with and serve to retract a portion of the patient's incised skin, the two halves of the patient's incised sternum and the patient's ribcage thereby exposing the coronary organs to be operated on through the resultant surgical window (labeled SW). The left and right sides of the retracted surgical incision (labeled LSI and RSI respectively) are schematically illustrated in FIG. 1A. When viewing the resultant surgical window SW from above the patient, the retractor arms 3 and 4 of the deployed surgical retractor 1 each have a generally arcuate orientation.

The sternum retractor 1 advantageously comprises arcuate rails 70 and 80 along the top of arcuate retractor spreader arms 3 and 4, respectively. The rails 70 and 80 configure an inverted T-slot arcuate passage 71 and 81, respectively, preferably centrally located within said rails, and preferably extending throughout the entire arcuate length of said rails. A similar linear longitudinal rail 50, may also be configured along the top of rack bar 5. Longitudinal rail 50 is also configured with an inverted T-slot longitudinal passage 51, preferably extending throughout its entire longitudinal length. These said rails form a mounting perimeter that can advantageously serve to engage a positioning and articulation mechanism utilized to place a variety of heart stabilizers during beating heart bypass surgery, for instance, as described in previously mentioned Canadian application Serial No. 2,216,893. Alternatively, the positioning and articulation mechanism may also be utilized to set a coronary organ contacting member used in cardiac surgery, such as a valve tissue retractor for example. As well, these rails can also be utilized to engage other surgical apparatus, that may need to be secured along the perimeter of the sternum retractor 1 during cardiac surgery.

A plurality of slit-like channels 72 and 82 are configured along the arcuate arms 3 and 4 and cut through the arcuate rails 70 and 80, respectively. FIG. 1A illustrates three such slit-like channels 72 on the retractor spreader arm 3 and three such slit-like channels 82 on the retractor spreader arm 4. The slit-like channels 72 and 82 extend downwards from the top of the rails 70 and 80 to a depth preferably below the entire depth of the inverted T-slot arcuate passages 71 and 81, preferably by an amount equivalent to the width of said slit-like channel. Similar slit-like channels were introduced in above mentioned Canadian patent application Serial No. 2,232,795, in order to provide passages for the placement of sutures serving to retract body tissue, for example pericardium tissue. The slit-like channels in the present invention and in Canadian application 2,232,795 are configured so that a suture line or other like wire-like filament will not restrict or otherwise hinder the functionality of the positioning and articulation mechanism when such mechanism becomes engaged in said passages 71 and 81 of said rails 70 and 80, provided the suture line or other wire-like filament is placed in the deepest position within said slit-like channel.

The sternum retractor 1 is configured with a plurality of anchoring ports 90, preferably disposed laterally outward away from the perimeter delineated by retractor arms 3 and 4, and consequently laterally outward away from the surgical window SW, in order to aim to maximize the access and visibility into the SW. For instance, the plurality of anchoring ports 90 can be configured laterally inward from the retractor arms 3 and 4, or configured as material extensions to retractor blades 7 and 8, but this would tend to compromise the ergonomics of the surgeon's workspace and access into the surgical window SW even though the slit-like channels 72 and 82 may be eliminated in this alternate configuration. It is also preferable to have each anchoring port 90 in line with each of slit-like channel 72 or 82, so that said anchoring port can conveniently serve to secure the tissue retractor 2 when at least a portion of the said tissue retractor is engaged in said slit-like channel.

The tissue retractor 2 is comprised of several main parts: (i) a tissue-piercing member such as a curved needle 20, (ii) a wire-like filament such as a suture line 23, (iii) an anchoring member such as anchoring plug 25, and (iv) an anchoring port 90. The curved needle is of a substantially circular cross-section having a sharp tip 201 suitable for piercing and penetrating body tissue, and a substantially blunt end 202 which is preferably integrally attached to the suture line 23 at point A. The material of both the suture line 23 and the curved needle 20 are as per existing suture lines and needles customarily used in surgery. The surgeon typically manipulates the needle 20 by grasping said needle between the jaws of a surgical needle holder, surgical clamp, or other surgical implement routinely used in surgery for manipulating the needle portion of traditional sutures. The anchoring plug 25 is also preferably integrally attached to the other end of suture line 23 at point F. Depending on the size of the surgical window SW required for the surgical intervention, the suture line 23 is of a suitable overall length, for instance between point A and F thereof, to permit retraction of the desired internal body tissue IBT by securing the tissue retractor 2 to the sternum retractor 1, in a manner that will be described in more detail below. The anchoring plug 25 further preferably incorporates a suture-locating slot 251 at its free end, whose function will be described in greater detail below. The longitudinal axis of the suture-locating slot 251 is preferably perpendicular to the longitudinal centerline axis of the anchoring plug 25.

Figure 1B:
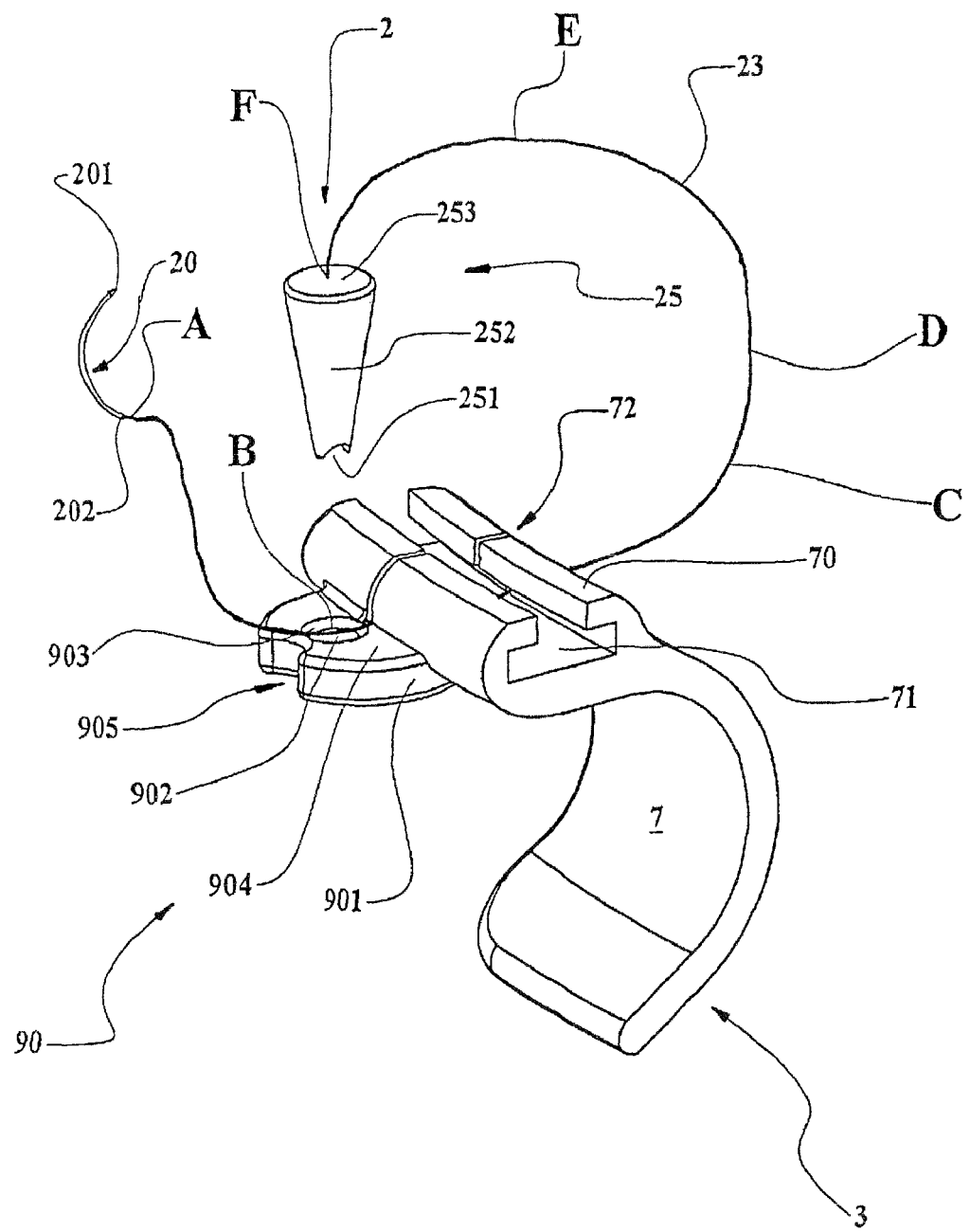
FIG. 1B is an exploded view of the suture and anchoring mechanism illustrated in FIG. 1A.
Figure 1C:
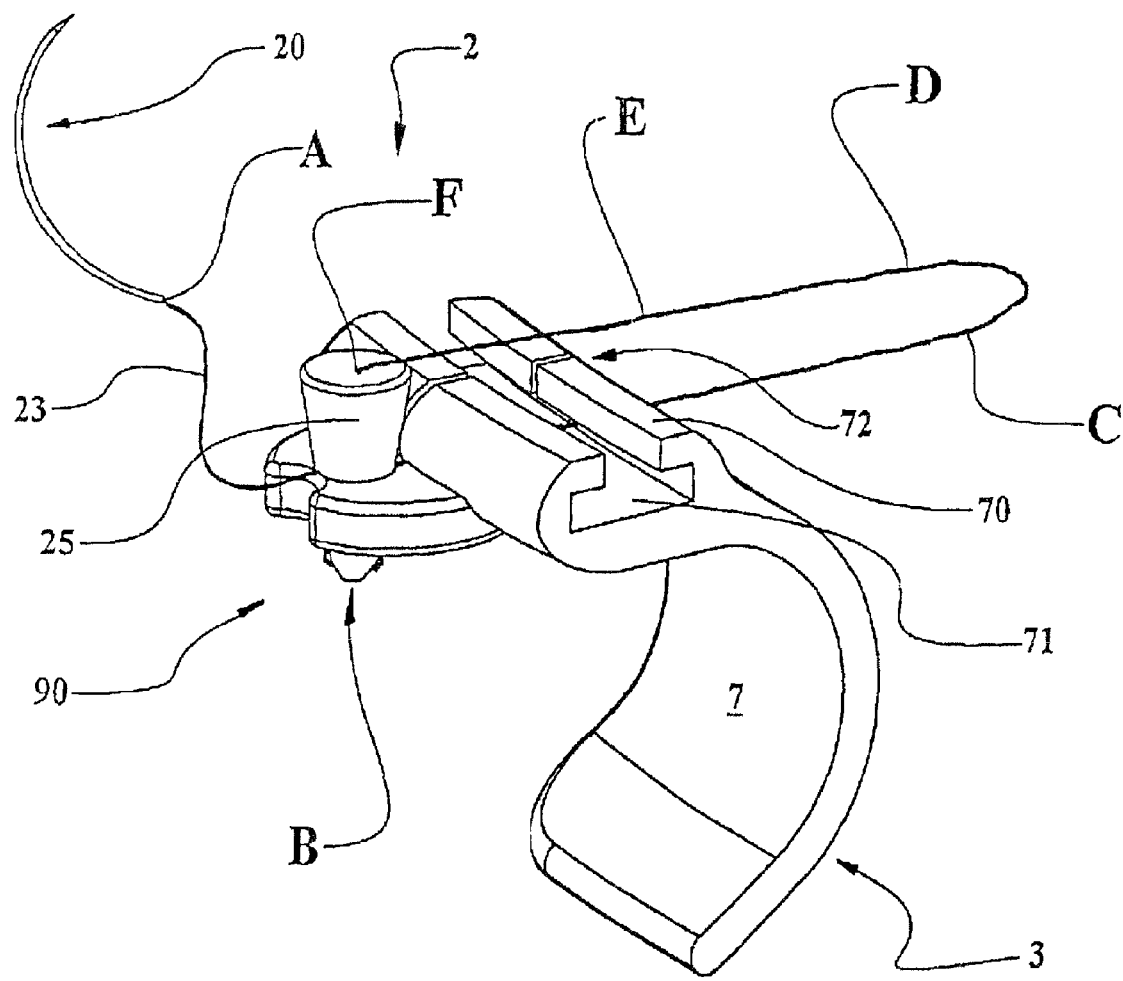
FIG. 1C is a partially assembled view of the suture and anchoring mechanism illustrated in FIG. 1B depicting a partially anchored suture line.
Figure 1D:
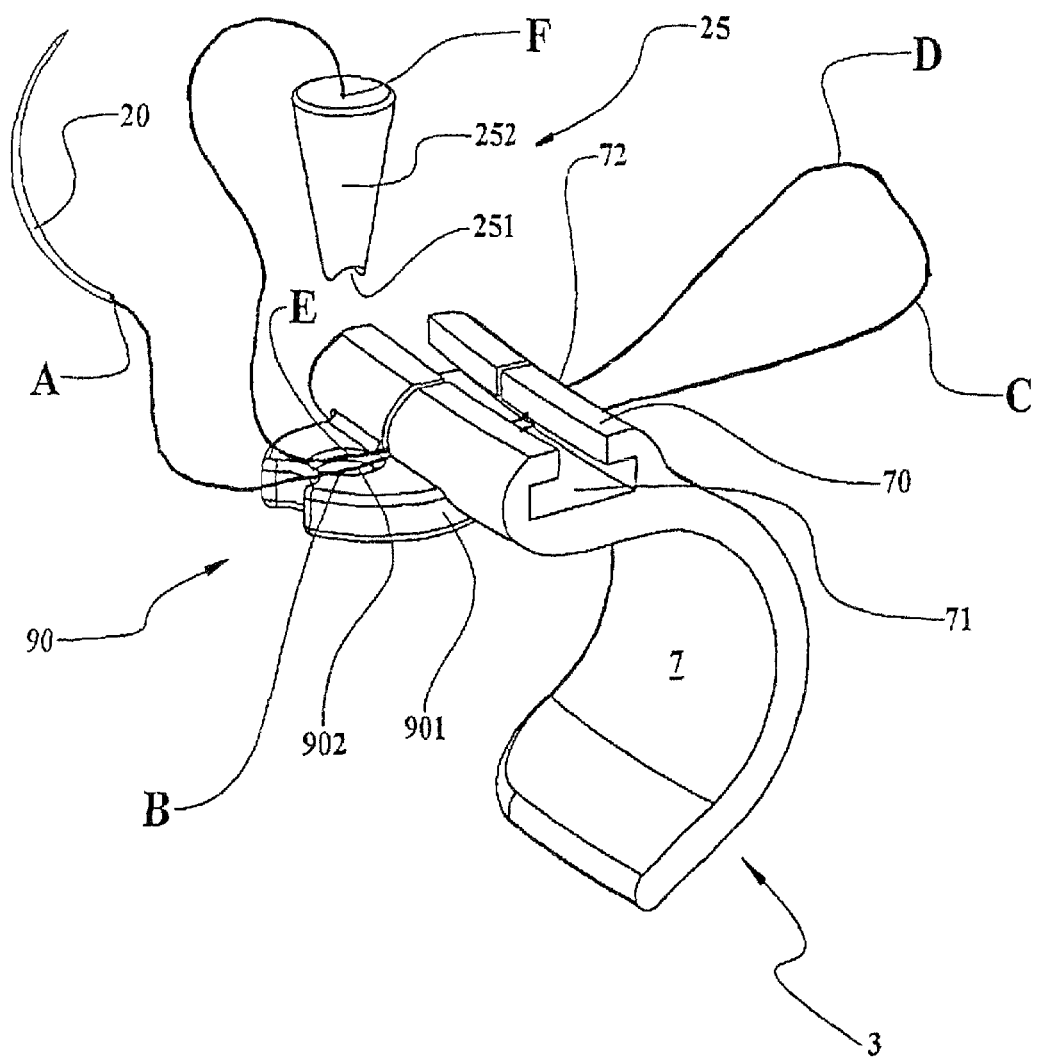
FIG. 1D illustrates a variant of the disposition of the suture line with reference to the first embodiment of FIGS. 1A to 1C.

In this first embodiment, as further illustrated in FIGS. 1B-1D, the anchoring port 90 is illustrated as being integral with the retractor arms 3, such as a cast boss, a brazed-on boss or a welded-on boss. Alternatively, the anchoring port 90 may also be a separate component that is mechanically fastened to the retractor arm 3 (or 4) by a variety of conventional fastening methods, such as bolting or riveting, in a manner that renders it fixed relative to the sternum retractor arm 3 (or 4) on which it is assembled, at least for the duration of the surgical intervention for which tissue retraction is performed. The anchoring port 90 in this embodiment is a substantially cantilevered fitting 901, disposed laterally outwards from the arcuate curvature of retractor arm 3 or 4, its top face 904 preferably having a substantially horizontal orientation when sternum retractor 1 is deployed in the patient. An aperture 902, preferably a through hole, is configured in the center of fitting 901, with the longitudinal axis of said aperture being preferably substantially vertical and substantially perpendicular to the laterally disposed, horizontally oriented fitting 901. Relative to the arcuate rail 70 (or 80), the top face 904 of the fitting 901 is situated below the maximum depth of slit-like channel 72.

The geometry of the aperture 902 can take on many variants (cylindrical aperture, conical aperture, tapered aperture, hexagonal cross section aperture, elliptical cross section aperture, and other geometries that will be apparent to those skilled in the art) but in all cases will depend on the geometry of the cooperating anchoring plug 25 which must remain secure relative to the anchoring port 90, and retractor arm 3 (or 4) on which said anchoring port is disposed, after the engagement of the anchoring plug 25 into the said port 90. A chamfer-like feature 903 is also preferably configured on the top surface 904 of fitting 901, around the perimeter of aperture 902, to ease the entry of anchoring plug 25 into aperture 902. In this embodiment, the anchoring plug 25 is defined by a substantially conical surface 252, truncated at its narrower free end by the surface defining the suture-locating slot 251. Preferably, the cross section of aperture 902 is progressively smaller in area, from its maximum area at the top surface 904 to a smaller area at its maximum depth in fitting 901, in order to promote wedging with the plug outer surface 252 when anchoring plug 25 is inserted and engaged into said aperture. The maximum diameter of the anchoring plug 25 is at least as large as the minimum diameter of aperture 902 so as to result in a substantially tight fit when said plug is engaged in said aperture. The maximum diameter of the anchoring plug 25 is preferably only slightly larger than the maximum diameter of the aperture 902, such that when said plug is fully engaged in said aperture, its top face 253 is located only slightly proud from fitting top face 904, with the result that the suture line 23 which is in tension from the retraction load it applies to the internal body tissue IBT is resting at the maximum depth within slit-like channel 72 in order not to interfere with the above mentioned positioning and articulation mechanism, or other surgical apparatus, which may be engaged or moved through the arcuate passage 71 (or 81).

FIG. 1C illustrates a partially engaged anchoring plug 25 within aperture 902. When the anchoring plug 25 will be fully engaged in aperture 902, the top face 253 will be substantially coincident with top face 904, thereby downwardly situating the length of suture line 23 between points F and D thereof such that the length of suture line 23 passing through the slit-like channel 72 will also come to rest at the maximum depth of said slit-like channel. This tends to ensure that the tissue retractor 2, and more specifically its suture line 23, is maintained in close proximity to the sternum retractor surfaces thereby aiding to improve the ergonomics of the surgical work site. When the anchoring plug 25 is fully engaged within aperture 902, the narrower free end of the anchoring plug and suture locating slot 251 extend below the fitting 901. Disengagement of the anchoring plug 25 from the anchoring port 90 is achieved by pressing upward on the suture locating slot 251, in a direction substantially parallel to the longitudinal axis of the aperture 902. The concavity of the suture locating slot 251 provides a groove for the surgeon's finger thereby tending to improve adherence while the disengagement load is applied. This said concavity may also be advantageously engaged with a surgical clamp, needle holder, or other surgical implement which may be used to apply the disengagement load.

In all the descriptions of embodiments according to the present invention, it is assumed that once the desired tissue retraction load is applied to the internal body tissue IBT, the tissue-piercing point of entry into the internal body tissue IBT (substantially coincident with point D on FIG. 1A and tissue-piercing point of exit out of internal body tissue IBT (substantially coincident with point C on FIG. 1A are situated below the plane formed across the top of arcuate rails 70 and 80 of a deployed sternum retractor 1 by at least the depth of the slit-like channels 72 and 82.

For purposes of illustrating the principles of the present invention, points A to F have been defined along the length of suture line 23. Point A is the extremity of suture line 23 attached to curved needle 201. Point F is the opposite extremity of suture line 23 attached to anchoring plug 25 or in some embodiments of the invention is the free end of suture line 23. Point C is the point along the length of suture line 23 located at the interface with internal body tissue IBT where the needle 20 exited therefrom during deployment of tissue retractor 2. Point D is the point along the length of suture line 23 located at the interface with internal body tissue IBT where the needle 20 pierced and entered into said internal body tissue IBT during deployment of tissue retractor 2. Point B is a point along the length of suture line 23 between point A and C to be selected for engagement with anchoring plug 25, or in later embodiments with a portion of other anchoring mechanisms. Point E is a point along the length of suture line 23 between point D and F to be selected for engagement with anchoring plug 25, or in later embodiments with a portion of other anchoring mechanisms. The relation of each points B, C, D, or E relative to each of points A or F is variable and arbitrary, depending in part on: the length of suture line 23 that is threaded through the internal body tissue IBT in a specific deployment of the tissue retractor 2; the thickness of internal body tissue IBT pierced by needle 20 that will contain a length CD of suture line 23 within internal body tissue IBT after threading of a length of suture line 23 occurs; and the portion of entire length of suture line 23 that will be selected for anchoring and securing tissue retractor 2 into anchoring port 90. A length AC of suture line 23 means the length of suture line between points A and C. A segment within length AC will mean a portion of suture line 23 between point A and point C substantially shorter than the total length between point A and point C.

In broad terms, a typical example of the surgical procedure for the set-up and deployment of the surgical apparatus relating to the present invention consists of the surgeon:

Grasping the needle 20 with a surgical needle holder close to the blunt end 202, pierce the internal body tissue IBT to be retracted or displaced with the needle tip 201 at the point of entry into said tissue;

a) Pushing said needle 20 through the internal body tissue IBT in a manner that the needle tip 201 exits through the internal body tissue IBT;

b) With the surgical needle holder, grasping the exposed portion of the needle 20 between the needle tip 201 and its point of exit from the internal body tissue IBT, and threading a length of suture line 23 through the internal body tissue IBT, for example a length between point A and point C on the suture line 23, also referred to as the threaded length AC (FIG. 1A-1B). A length between point C and point D of suture line 23 remains contained within the internal body tissue IBT, and will also be referred to as the bearing length CD, and a length between point D and point F of suture line 23 is not threaded through the internal body tissue IBT, and will also be referred to as unthreaded length DF;

c) Pulling on the two lengths AC and DF simultaneously and sufficiently to effectuate and maintain the desired internal body tissue IBT retraction, or to effectuate and maintain the desired displacement of the internal body tissue IBT from its anatomical disposition, or to effectuate and maintain the desired displaced position or displaced orientation of a body organ through the retraction of internal body tissue IBT that is anatomically attached to said body organ;

d) While maintaining the pulling loads on the two lengths AC and DF for the desired internal body tissue IBT retraction (one length in each hand), insert a segment within length AC of suture line 23 into slit-like channel 72 (or 82) and over the opening of aperture 902 of one of the anchoring ports 90 disposed on sternum retractor 1, (point B of suture line 23 is at this point situated over aperture 902—FIG. 1C);

e) While maintaining the pulling loads on the two lengths AC and DF for the desired internal body tissue IBT retraction, bring the suture-locating slot 251 of anchoring plug 25 in contact with the segment of suture line 23 at point B over aperture 902, and insert and engage the anchoring plug 25 into said aperture 902 with a downward force thereby securing the desired internal body tissue IBT retraction or displacement according to (d);

f) if required, readjust the magnitude of retraction applied to the internal body tissue IBT or readjust the magnitude of displacement exerted on the internal body tissue IBT by first disengaging anchoring plug 25 from aperture 902 and re-engage by repeating steps (d) to (f) above, with a different pulling force to effectuate and maintain the desired readjustment in internal body tissue IBT retraction or displacement;

g) if required, readjust the direction of retraction load applied to internal body tissue IBT or readjust the direction of displacement exerted thereon by first disengaging anchoring plug 25 from existing aperture 902 and re-engage said anchoring plug into another anchoring port 25 forming part of the plurality of such anchoring ports, by repeating steps (d) to (f) above.

FIG. 1C illustrates one of the ways tissue retractor 2 can be deployed, as outlined above in broad terms. FIG. 1C illustrates the anchoring plug 25 in the partially inserted position with the aperture 902. Only a segment within length AC of suture line 23 is engaged into slit-like channel 72 and another segment of suture line 23 in the vicinity of point B is pressed through the opening of aperture 902 by virtue of this latter segment's engagement within suture-locating slot 251. The suture line 23 of tissue retractor 2 is secured in a substantially fixed relation to the anchoring port 90 by the action of sufficiently pressing down on and wedging the anchoring plug 25 into aperture 902, in a manner to pinch or trap the segment of suture line 23 that is engaged between the outer surface 252 of plug 25 and surface of aperture 902, thereby maintaining the desired internal body tissue IBT retraction load or displacement. The deployment of tissue retractor 2 is now complete. It is preferable in this method of deploying tissue retractor 2 that each of the lengths AC and DF of suture line 23 is held by a separate hand until the tissue retractor 2 is fully engaged with the anchoring port 90, and its deployment complete. With the suture line 23 in tension from the retraction load the surgeon applies to the internal body tissue IBT, and with a segment within length AC of suture line 23 engaged in slit-like channel 72, a V-notch 905 in fitting 901 serves advantageously to align a segment within length AC of suture line 23 over the opening of aperture 902 poised to receive the suture-locating slot 251 of plug 25 when said plug is inserted in aperture 902 with another hand.

FIG. 1D illustrates an alternate method of deployment of tissue retractor 2 in anchoring port 90. The anchoring plug 25 is shown prior to its insertion into aperture 902. Unlike the previous method of deployment described above in reference to FIG. 1C, both lengths AC and DF of suture line 23 are held by the surgeon in one hand, preferably between point A and B on one length and between point E and F on the other length, after the internal body tissue IBT is pierced with needle 201 and a portion of suture line 23 denoted as length CD thereof is contained within internal body tissue IBT. The surgeon pulls on both lengths AC and DF simultaneously with one hand to apply and maintain the desired retraction or displacement of the internal body tissue IBT, while inserting a segment within length AC and a segment within length DF in slit-like channel 72. Also by this action, a segment within length AC in the vicinity of point B and a segment within length DF in the vicinity of point E are disposed over aperture 902, ready to receive suture-locating slot 251 of anchoring plug 25 as said plug is inserted in aperture 902 and engaged with anchoring port 90 by the action of the other hand. Like in the previous method of deployment, the suture-locating slot 251 serves to locate the portions of suture line 23 it contacts in a substantially diametric orientation with respect to the free end of plug 25. The suture line 23 of tissue retractor 2 is secured in the same manner as in the first method of deployment described above, with the exception that two segments of suture line 23 (one in the vicinity of point B and the other in the vicinity of point E) will be pinched or trapped between the outer surface 252 of plug 25 and the surface of aperture 902, thereby maintaining the desired internal body tissue IBT retraction load or displacement.

Adjustment of the magnitude of the retraction force exerted on the internal body tissue IBT or the magnitude of displacement of the internal body tissue IBT from its original position in the body is accomplished by disengaging anchoring plug 25 from the anchoring port 90, thereby freeing the trapped segment or segments of suture line 23, and re-inserting and re-engaging said plug 25 into said port 90 in such a manner as to trap or fix a different segment or segments of suture line 23. Trapping or fixing a segment of suture line 23, within length AC, that is closer to point C (or simultaneously fixing a segment of suture line 23 within length AC that is closer to point C and another segment within length FD that is closer to point D) will result in an increase in displacement of internal body tissue IBT from its original position within body, and usually also result in an increase in the retraction load applied to achieve such displacement.

Adjustment of the direction of the tissue retraction force exerted by the suture line 23 on internal body tissue IBT is accomplished by removing anchoring plug 25 from the anchoring port 90, thereby freeing the trapped segment or segments of suture line 23, and re-inserting the said plug 25 into another anchoring port 90 situated at a different location on the sternum retractor 1 in such a manner as to trap a different segment or simultaneously different segments of the suture line 23. This effectively changes the orientation of the suture line 23 with respect to the internal body tissue IBT, and consequently the direction of the retraction force applied to the internal body tissue IBT. Adjustment of both the magnitude and direction of the retraction force is possible by simultaneously moving anchoring plug 25 and suture line 23 into another anchoring port 90 and by varying the suture length BC and DF (first method of deployment) or BC and DE (second method of deployment) between the internal body tissue IBT and the anchoring port 90.

In both methods of deployment of the tissue retractor 2 illustrated in FIGS. 1C and 1D, the desired retraction or displacement of the internal body tissue IBT is accomplished without the need to manually tie down suture lines in the manner previously explained. In both said methods of deployment, adjustment of the magnitude of retraction of displacement of the internal body tissue IBT or adjustment of the direction of retraction load applied on the internal body tissue IBT or its direction of displacement may be accomplished without having to dispose of existing suture and re-piercing the internal body tissue IBT with a newly deployed suture.

As mentioned in the description of this first embodiment, and as illustrated in FIGS. 1A-1D, the fitting 901 preferably assumes a substantially horizontal orientation, and the longitudinal axis of aperture 902 is preferably substantially vertical. Alternatively, the fitting 901 can assume an orientation that is other than horizontal, or the longitudinal axis of aperture 902 can assume a non-vertical orientation, or even both the fitting 901 orientation and aperture 902 orientation may be varied simultaneously, while still maintaining the principles and obtaining the desired results of the present invention as described above.

In this first embodiment according to the present invention, the anchoring port 90 and the anchoring plug 25 cooperate and together serve as an anchoring mechanism. A variety of geometries for the anchoring port 90 and anchoring plug 25 are possible which serve the intended purpose of trapping, wedging, clamping, pinching, or otherwise substantially fixing a segment of the suture line 23 relative to a substantially stable surgical platform, such as a sternum retractor 1. FIGS. 2A to 2C illustrate a few geometric variations for the said anchoring plug. FIG. 2A illustrates a tapered anchoring plug 26 with a multitude of substantially circumferential ridges 261 spaced along plug outer surface 262. Two adjacent ridges 261 serve to trap a segment of suture line 23 therebetween, and at least one of the said ridges serves to pinch the two endpoints of said trapped segment between the surface of ridge 261 and the surface of aperture 902, when anchoring plug 26 is fully engaged in anchoring port 90. FIG. 2B illustrates a tapered anchoring plug 27 comprised of a series of progressive conical wedges 271. FIG. 2C illustrates a tapered hexagonal anchoring plug 28. For each of these variant anchoring plug geometries, the corresponding aperture 902 geometry must cooperate with these said plug geometries to achieve the intended use of substantially fixing the segment of suture line 23 engaged within aperture 902 relative to the sternum retractor 1, thereby maintaining the tensile retraction load in the suture line 23 and the desired internal body tissue IBT retraction. For example, the said aperture cooperating with hexagonal anchoring plug 28 is also preferably substantially hexagonal in cross section tending to improve the fit between said cooperating components. The anchoring plugs 25,26,27 and 28 shown in the preceding figures are preferably manufactured in a polymer or substantially rubber-like compound in order to tend to improve their conformance and adherence to the mating geometry of cooperating aperture 902. The said anchoring plugs may be at least partially elastic, partially malleable, or partially compliant in the sense that at least those portions of the anchoring plugs which contact the cooperating aperture will exhibit the desired characteristics of elasticity, malleability, or compliance. With such a construction, the said anchoring plugs are typically not well-suited for conventional steam sterilization and are typically disposable elements. In addition to having a geometry to suit the said anchoring plug geometry of specific variants, the surfaces of the said aperture can be manufactured or coated with a surface texture to further enhance friction, fit, or adherence with the engaged said anchoring plug.

In this first embodiment the components comprising the tissue retractor 2, for instance is the curved needle 20, the suture line 23, and the anchoring plug 25 form an integral assembly, which can be advantageously packaged in sterilized packets similar to standard suture packets. This integral assembly would be a single use disposable implement as is the case with existing sutures. The components comprising the anchoring port 90, which may be either integral or mechanically assembled to a surgical platform such as a preferably reusable sternum retractor 1, would also be preferably reusable. As explained below, the tissue retractor 2 offered in disposable form and available in ready-to-use sterilized packets also provides the possibility for classifying some of the variables of the tissue retractor configuration. For instance, the tissue retractor can be offered in a variety of classified suture line 23 lengths, a variety of classified suture line 23 materials, a variety of classified suture line 23 widths, a variety of tissue-piercing needle 20 configurations, to name but a few examples. This allows the surgeon to select the most suitable sterilized packet to perform the specific tissue retraction operation, similar to the current classification and selection practice that is followed with traditional surgical sutures. In another variant, the suture line 23 with integral needle 20 is offered as traditional disposable suture, and the anchoring plug is a separate reusable component, manufactured in metal, and endowed with compliant properties by virtue of its mechanical design in order to aim to enhance its fit and cooperation with the aperture geometry. In another variant, the needle 20 can be detachable from the suture line 23 at point A, after the tissue retractor 2 is completely deployed, in order to remove the risk of having a sharp tip 201 exposed during the surgical intervention.

FIGS. 3A-3C illustrate further variants of tissue retractor 2 by replacing anchoring plug 25 with anchoring plugs 29, 30 or 31 that include handle members 291, 301 and 311, respectively. Handle members 291, 301 and 311 tend to facilitate the manipulation of said anchoring plugs 29, 30 and 31 especially with regards to insertion and removal of said plugs from anchoring port 90, by either a human hand or through the use of a surgical implement. Suture line 23 is attached to said handle members at point A, preferably along the central longitudinal axis defining said anchoring plugs. The said handle members are preferably configured with circular outer profiles 293, 303 and 313, but may also be configured with other non-circular outer profiles suitable to facilitate manipulation of said anchoring plugs. The handle members 291, 301, 311 are also preferably manufactured integral with the anchoring plugs 29, 30, 31. FIG. 3A illustrates a basic disc shaped handle member 291; FIG. 3B illustrates a disc shaped handle member 301 with integral traction ridges 302 tending to reduce slippage during manual manipulations, especially with wet surgical gloves; FIG. 3C illustrates an annular handle member 311 permitting the insertion of either a human finger or surgical implement through opening 312 to tend to facilitate disengagement of plug 31 from anchoring port 90.

The said handle members may also advantageously serve to allow the surgeon to apply a rotation, about the longitudinal axis of the said anchoring plug, at some point during the insertion procedure of said anchoring plug into anchoring port 90, before the complete deployment of the tissue retractor is accomplished. This enables an anchoring plug with a circular cross-sectional area (in a plane perpendicular to its longitudinal axis) except for a local raised dimple or longitudinal bulge along its outer surface, to be easily inserted in one discrete orientation relative to the anchoring port 90 by virtue of the aperture 902 having a volumetric provision to accommodate said dimple or said bulge in said discrete orientation relative to anchoring port 90. Rotation of the handle member can serve to compress anchoring plug across its dimple or bulge, as anchoring plug is forced to assume a new orientation within anchoring port 90 whereby said volumetric provision in said aperture opening is no longer engaged by the anchoring plug dimple or bulge. This rotation thereby tends to secure the anchoring plug within the anchoring port, and with a segment of suture line 23 pinched between said plug and said aperture, the intended purpose of the invention is fulfilled.

Figure 4B:
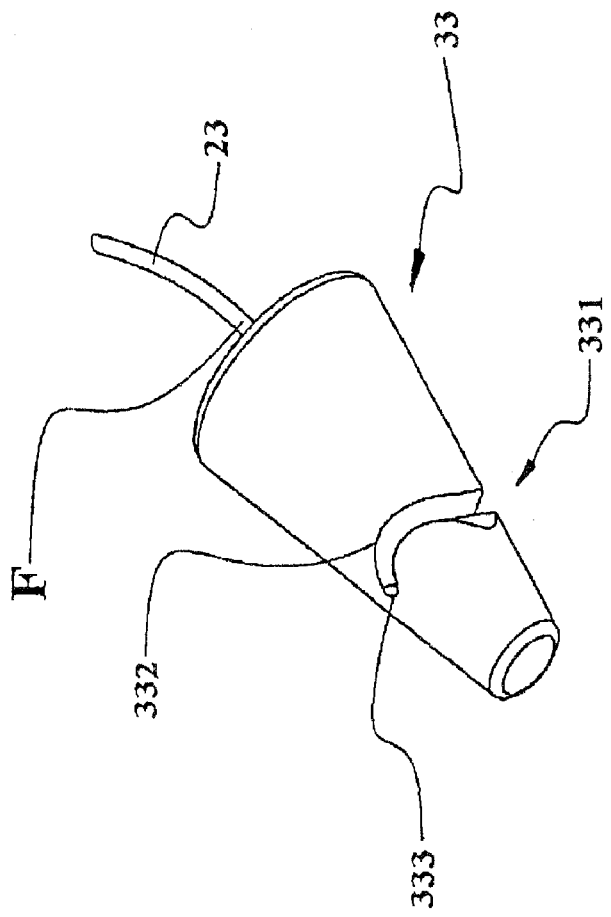
FIGS. 4A and 4B illustrate variants of anchoring members of the anchoring mechanism with reference to the first embodiment of FIGS. 1A to 1D, comprising openings therein suitable for reception of a suture line.
Figure 4A:
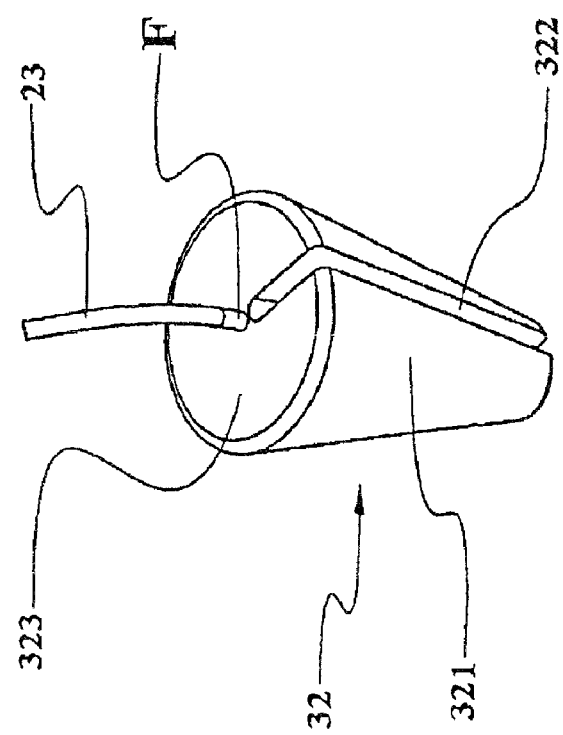

FIG. 4A illustrates a further variant of tissue retractor 2 by replacing anchoring plug 25 with anchoring plug 32. Like the previous embodiments, anchoring plug 32 preferably forms an integral assembly with suture line 23 which originates from its top face 323, and curved needle 20 attached to other end of suture line 23 (not shown). Anchoring plug 32 is advantageously manufactured with a longitudinal slot 322 preferably extending along the entire length of said plug. The outer surface 321 of plug 32, in its free unconstrained state prior to its insertion and engagement with anchoring port 90, defines a cross section (transversely to plug longitudinal axis and neglecting cross section of slot 322) that is substantially larger than the cooperating transverse cross section in aperture 902. The material of the plug is substantially elastic or substantially malleable such that when said plug 32 is inserted and engaged in aperture 902, the outside surface 321 will be compressed and constrained into assuming a smaller cross section, due largely to the resulting narrowing of circumferential width of slot 322. Consequently, a segment within length AC of suture line 23 (or a segment within length AC and segments within length DF of suture line 23) engaged within slot 322 will be clamped by the opposing surfaces defining slot 322. The suture line 23, loaded in tension by the retraction load it applies to the internal body tissue IBT, will thereby be fixed relative to the completely engaged plug 32 in port 90, and thereby tending to maintain the desired internal body tissue IBT retraction. This configuration of anchoring plug 32 may be advantageous in tending to reduce slippage and tending to increase the pinching or clamping force exerted on the suture line 23 to keep the engaged length of said suture line fixed or secured relative to the anchoring plug 32 and anchoring port 90. Adjustment of the magnitude of the retraction force exerted by the suture line 23 on the internal body tissue IBT or the magnitude of displacement of the internal body tissue IBT from its original position in the body is accomplished by disengaging anchoring plug 32 from port 90 and displacing through slot 322 at least one of the engaged segments of suture length 23 to thereby engage a different segment of suture line 23. Adjustment of the direction of the tissue retraction force exerted by the suture line 23 on the internal body tissue IBT is accomplished by disengaging plug 32 and re-engaging said plug into another anchoring port 90 situated at a different location on the sternum retractor 1, in such a manner as to clamp different segments of suture line 23 in the manner described above. The inner surfaces of longitudinal slot 322 can be substantially smooth, as illustrated in FIG. 4A, or alternatively can be textured, rough or serrated to tend to increase the friction force exerted on engaged suture line 23 when it is clamped between said surfaces during engagement of plug 32 into port 90. The slot 322 is illustrated in a substantially longitudinal configuration relative to plug 32 but may alternatively assume a substantially helical disposition about the longitudinal axis of said plug 32.

FIG. 4B illustrates a further variant of tissue retractor 2 by replacing anchoring plug 25 with anchoring plug 33 and, like the previous embodiments, preferably forms an integral assembly with suture line 23 and curved needle 20 (not shown). Plug 33 is configured with a suture-locating slot 331 substantially transverse to the longitudinal axis of the plug 33. Relative to suture-locating slot 251 of the first embodiment, slot 331 tends to improve the cooperation of plug 33 with the engaged segment or segments of suture line 23 during insertion and removal of said plug into anchoring port 90. During insertion of plug 33 into anchoring port 90, the engaged segment of suture line 23 is in contact with concave surface 332 of said slot 331. During disengagement of plug 33 from port 90, the engaged segment of suture line 23 is in contact with concave surface 333 of said slot 331. Unlike the first embodiment illustrated in FIG. 1A-1D, when plug 33 is fully engaged in port 90, the engaged segment or segments of suture line 23 located within slot 331 are contained within the surfaces defining aperture 902, and said engaged segment or segments are not exposed below the fitting 901 as is the case in this first embodiment where suture locating slot 251 is configured on the free end of plug 25. Alternatively, slot 331 may be replaced by a substantially transverse hole. In this variant, after the internal body tissue IBT tissue is pierced and a length AC of suture line 23 threaded through said internal body tissue IBT, the curved needle 20 is then inserted through said hole along with a length AB of suture line 23 which is also threaded through said hole prior to insertion and engagement of anchoring plug in anchoring port 90.

In the remaining embodiments, the portion of the internal body tissue IBT that is pierced by needle 20 and threaded by suture line 23 is not illustrated. However, if illustrated the internal body tissue IBT would contain and shield length CD of suture line 23, also previously defined as the bearing length CD. Point C is the point along the length of suture line 23, of a fully deployed tissue retractor 2, that lies at the point of exit of said suture line 23 from the retracted internal body tissue IBT. Point D is the point along the length of suture line 23, of a fully deployed tissue retractor 2, that lies at the point of entry of said suture line 23 into the retracted internal body tissue IBT.

Figure 5A:
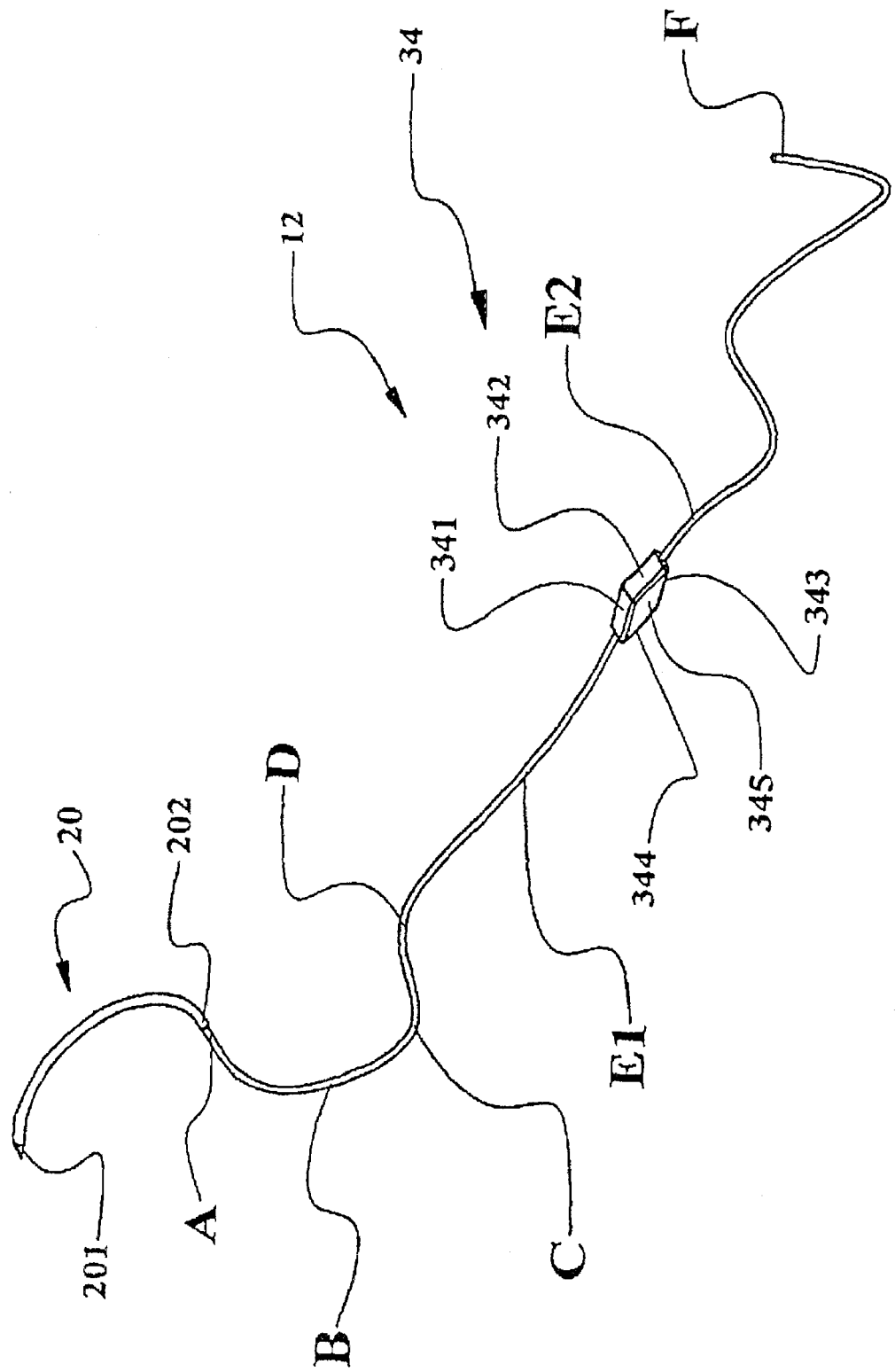
FIGS. 5A and 5B illustrate a tissue retractor comprising a suture and associated anchoring mechanism according to a second embodiment of the present invention.
Figure 5B:
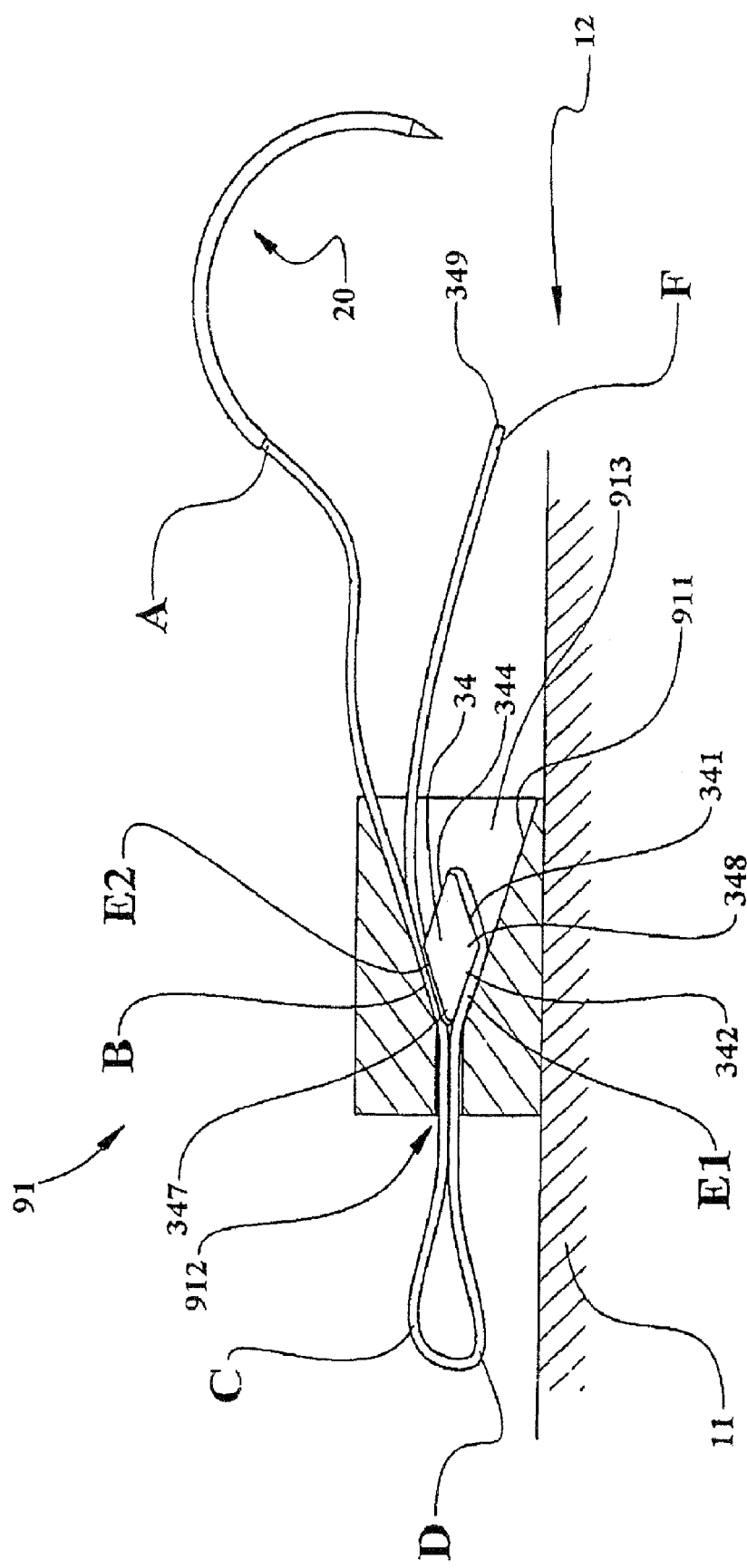

FIG. 5A illustrates a second embodiment according to the present invention. The tissue retractor 12 is comprised of a tissue-piercing member such as a curved needle 20, a wire-like filament such as a suture line 23, an anchoring member such as anchoring plug 34, and an anchoring port 91. Unlike the first embodiment, the anchoring plug 34 in this second embodiment is not rigidly attached to the suture line 23 at a fixed location along its length, but is slidingly engaged to said suture line 23 and thereby capable of assuming any location along the entire length AF of suture line 23. Anchoring plug 34 is substantially diamond-shaped with substantially planar faces 341, 342, 343, and 344 forming the suture-contacting perimeter of said diamond shape. A suture guide passage 346 extends through anchoring plug 34, and is of a suitable width dimension to allow insertion of suture line 34 through said passage 346. The longitudinal axis of passage 346 substantially bisects the wedge angle formed by face 341 and 344, and also by face 342 and 343. Preferably, the assembly fit that results between the inserted portion of suture line 23 and passage 346 is not loose, and the force required to slide the anchoring plug 34 along at least a length of suture line 23 may be easily overcome by the manual force applied by surgeon. Once the anchoring plug 34 is inserted on the suture line 23, the width of the suture line 23 at its free end 349 is preferably enlarged to prevent plug 34 from disengaging suture line 23 during subsequent manipulations or deployment of tissue retractor 12. This may be achieved either through the formation of a knot placed in suture line 23 in the vicinity of its free end 349, or alternatively during the manufacturing process of tissue retractor 12 when an end fitting, such as a spherical end cap (not shown) of larger width dimension than suture line 23 can be permanently mounted to the said free end 349. Cooperating with anchoring plug 34 to accomplish the desired internal body tissue IBT retraction is anchoring port 91. FIG. 5B schematically illustrates a substantially rigid and substantially stable platform 11, for instance at a location on the sternum retractor 1, onto which is disposed anchoring port 91. FIG. 5B also schematically represents a top view of a sectioned anchoring port 91. Port 91 is configured with a narrow slit-like channel 912, which may also be an extension of slit-like channel 72 in outward direction from surgical window SW. In moving outwardly relative to surgical window SW, the faces defining the width of slit-like channel 912 diverge to form a wedge shaped aperture 914 defined by two diverging faces 911. Surface 913 forms the bottom face of slit-like channel 912 and the bottom face of wedge aperture 914, thereby also serving as a location datum for lateral faces 345 of anchoring plug 34, when said plug is engaged in said port. The geometry of the wedge aperture 914 and the geometry of diamond shape anchoring plug 34 substantially coincide to properly cooperate during the deployment of the tissue retractor 12.

FIG. 5B illustrates a fully engaged tissue retractor 12 within wedge shaped aperture 914, according to a first preferred method of deployment. As previously explained, the anchoring plug 34 may be manufactured in a material or design that makes it at least partially malleable or partially elastic to tend to improve its conformity to cooperating faces 911 and its compliance around the engaged suture line that it will pinch against faces 911. In broad terms, this preferred method deployment for this second embodiment according to the present invention, consists of:

a) piercing the internal body tissue IBT with needle 20 and threading a length AC of suture line 23 through said internal body tissue IBT;

b) retracting pierced internal body tissue IBT by simultaneously pulling on both lengths AC and DF of suture line 23;

c) selecting the most convenient anchoring port 91 from the plurality disposed around sternum retractor 1, estimating the required location of anchoring plug 34 along suture line 23 to be able to secure the desired internal body tissue IBT retraction by engagement of anchoring plug 34 into the selected anchoring port 91;

d) sliding the anchoring plug 34 along suture line 23 to the said required location;

e) in length DF of suture line 23 (between internal body tissue IBT and free end 349), rotating the diamond shape anchoring plug 34 such that point E1 on suture line 34 comes in contact with face 342, and point E2 comes in contact with face 343;

f) bringing length AC of suture line 23 (between internal body tissue IBT and needle 20) in contact with anchoring plug 34 such that point B comes in contact with face 343;

g) while holding anchoring plug 34 in the relationship described in (f) above, simultaneously pulling on both lengths of suture line 23, preferably between point B and C on one length and point D and E1 on the other length, to exert the desired internal body tissue IBT retraction;

h) while maintaining the desired internal body tissue IBT retraction, inserting simultaneously a portion of each length BC and DE1 in slit-like channel 912, and also inserting anchoring plug 34, with the above said relationship to suture line, in wedge aperture 914 (lengths E2F and AB of suture line 23 extending beyond port 91 preferably in outwardly direction from surgical window SW);

i) releasing anchoring plug 34;

j) if required, readjusting the magnitude of retraction load exerted on internal body tissue IBT by first pulling simultaneously on lengths BC and DE1 of suture line 23, in a manner to increase retraction load slightly thereby loosening wedging action between plug 34 and port 91. Secondly disengaging plug 34 from port 91 and repeating steps (b) to (h) above;

k) if required, readjusting the direction of retraction load applied to internal body tissue IBT or readjusting the direction of displacement exerted on internal body tissue IBT by performing step (j) above but only re-engaging anchor 34 into another port 91 located along the perimeter of sternum retractor 1.

In this preferred method of deployment, the tensile load in length BC and DE1 of suture line 23, due to the retraction exerted on internal body tissue IBT, tends to wedge diamond faces 343 and 342 into wedge faces 911 of port 91 thereby pinching or clamping suture line engaged between 911 and said wedge diamond faces. In addition, this said tensile load in length BC and DE1 tends to impart a moment on anchoring plug 34 and rotate it in a clockwise direction as it is illustrated in FIG. 5B, within wedge aperture 914. This tends to increase the pinching action by anchoring plug 34 on engaged suture line 23, especially at corner locations 347 and 348. Suture-contacting perimeter faces 341, 342, 343, or 344 may be textured, rough or serrated to tend to increase the friction force exerted on engaged suture line 23 when it is clamped between some of the said perimeter faces and faces 911 of wedge aperture 914, which may also be textured.

A second alternate method of deployment (not illustrated), in broad terms, consists of eliminating step (e), that is, eliminating the rotation of diamond plug 34 so that E1 is in contact with 342 and E2 is in contact with 343. In this second method, point B is in contact with perimeter face 341 but length DF passes directly through passage 346 without being wrapped around any of the perimeter faces 341, 342, 343, or 344. In this method of deployment, it is preferable to have an anchoring plug 34 configured with a longitudinal slit through one of the side faces 345, preferably in communication with the entire length of passage 346. This configuration attempts to augment the clamping force on the length of suture line 23 engaged in passage 346 by virtue of the wedging action on faces 343 and 342 transmitting a closing force across this said longitudinal slit. Therefore, in this method of deployment length AC is pinched or clamped at location B between face 341 and wedge face 911 of aperture 914 and the other length DF is clamped over the engaged length contained in passage 346, that falls between points E1 and E2.

Figure 5D:
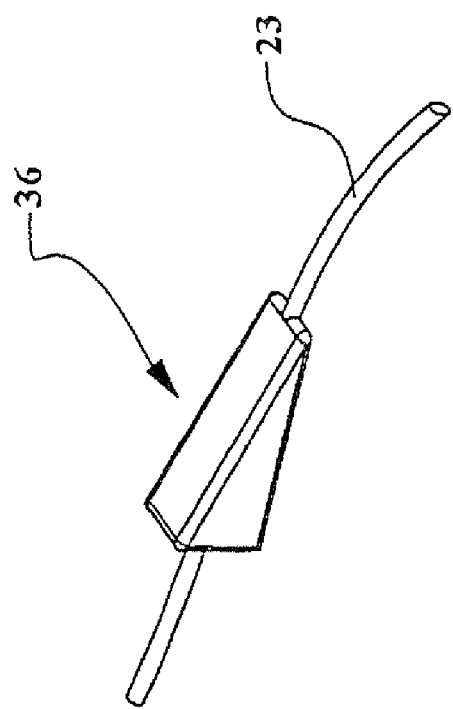
FIGS. 5C and 5D illustrate several variants of anchoring members of the anchoring mechanism with reference to the second embodiment of FIGS. 5A and 5B.
Figure 5C:
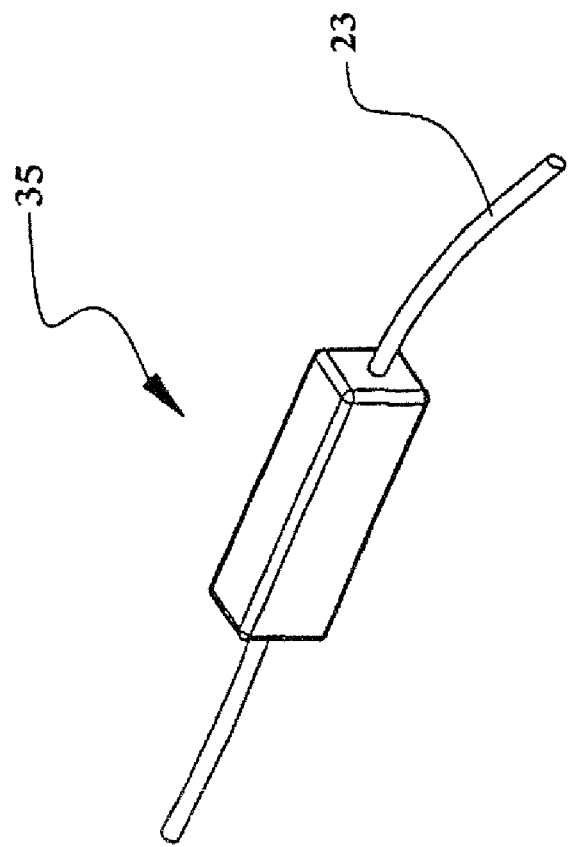

In this second embodiment according to the present invention, the anchoring port 91 and the anchoring plug 34 cooperate and together serve as an anchoring mechanism. Other geometric variations of the anchoring plug 34 and the cooperating anchoring port 91 are possible without departing from the spirit of this second embodiment. FIGS. 5C and 5D illustrate two such variations; a rectangular-shaped plug 35 is shown in FIG. 5C while a triangular wedge-shaped plug 36 is shown in FIG. 5D. Other geometric variations for the anchoring plug may include an elliptical-shaped anchoring plug. All these variants may be deployed in at least one of the methods of deployment described above.

Figure 6A:
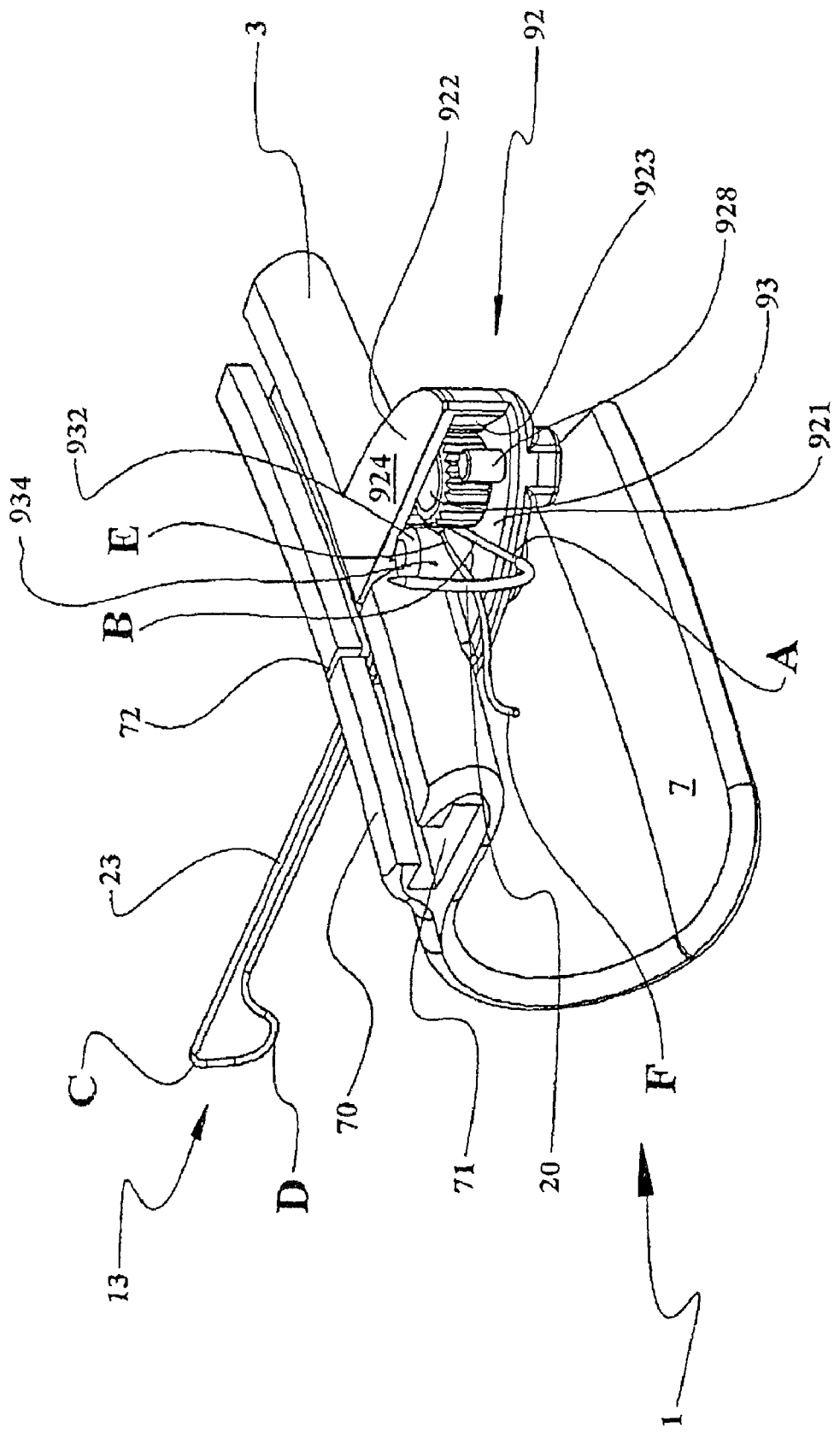
FIG. 6A is a perspective view illustrating a tissue retractor comprising a suture and associated anchoring mechanism according to a third embodiment of the present invention.

FIG. 6A illustrates the third embodiment according to the present invention. Internal body tissue IBT retraction will be effectuated with a traditional suture 13, comprised of a curved suture needle 20 and a suture line 23, that becomes engaged with anchoring mechanism 92 disposed on sternum retractor 1, in a plurality of locations similar to the disposition of anchoring ports 90 of the first embodiment. FIG. 6A illustrates only the most remote portion relative to rack bar 5 of retractor spreader arm 3, with one anchoring mechanism 92 disposed laterally outward on said arm 3.

Anchoring mechanism 92 is comprised of the following components: a housing 922, a pinch roller 934, a traction roller 93, a retention pin 928, and a shoulder bolt 932. The housing 922 may be either an integral extension of retractor arm 3 (or 4) or may be mechanically fastened to said retractor arm to form a rigid assembly during at least the duration of the surgical intervention requiring tissue retraction.

Figure 6B:
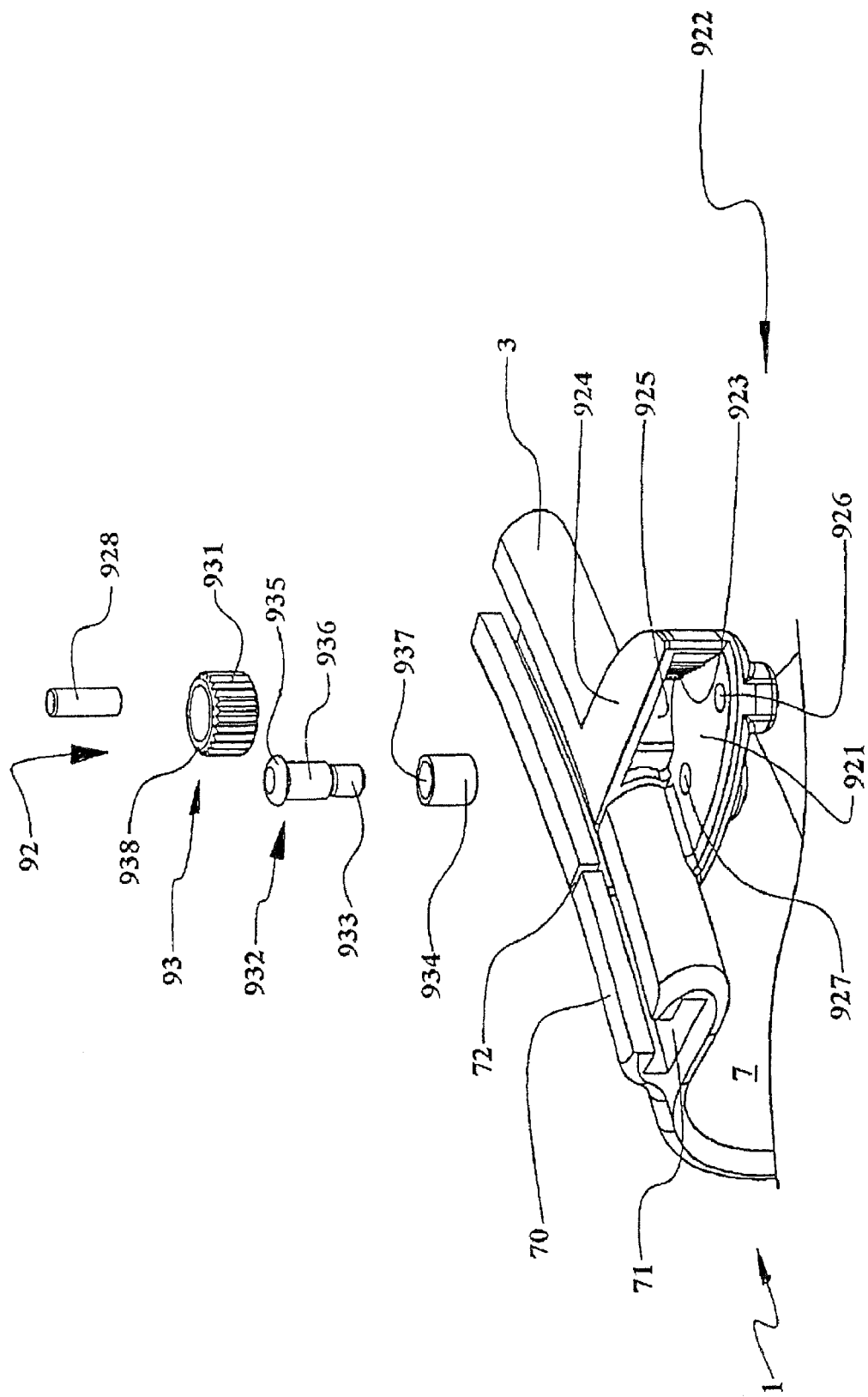
FIG. 6B is an exploded view of the anchoring mechanism according to the third embodiment of the present invention illustrated in FIG. 6A comprising a pinch roller member and traction roller member.

Housing 922, serving to retain or to partially house the cooperating components of anchoring mechanism 92, is defined by: a base platform 921 which disposes threaded hole 927 for engagement of shoulder bolt 932 and hole 926 for engagement of retention pin 928 (FIG. 6B); a wall member 925 (FIG. 6B) which is configured with traction surface 923 over at least a portion of its entire surface; and a top plate 924. A substantially tubular pinch roller 934 is mechanically assembled to the base platform 921 by shoulder bolt 932, whose thread 933 engages with threaded hole 927 (FIG. 6B), said shoulder bolt rigidly engaged to base platform 921 after assembly. Axial movement of pinch roller 934 is limited in one direction by the shoulder 935 and in the other direction by platform 921. Lateral movement of pinch roller 934 (i.e. perpendicular to its centerline) is limited by the clearance between the outer diameter of shank 936 and inner diameter 937 of pinch roller 934. This said clearance is preferably minimized but sufficient to allow pinch roller 934 to rotate freely about its centerline relative to shoulder bolt 932. Cylindrical traction roller 93, with traction ridges 931 configured on its circumferential surface, is subsequently inserted into the slot created by top plate 924 and base platform 921. A cylindrical retention pin 928 is subsequently inserted into hole 926 (FIG. 6B), and preferably permanently fixed in said hole, either by a staked mechanical press fit, brazing, welding, or riveting for instance, in order to permanently trap traction roller 93 within anchoring mechanism 92. In the same manner, threaded shoulder pin 932 may be replaced by a stepped shoulder pin that is also permanently fixed to housing 922 after having been inserted through pinch roller 934, in order to permanently trap pinch roller 934 to housing 922. This open configuration of anchoring mechanism 92 as illustrated in FIG. 6A tends to facilitate sterilization and cleaning of this surgical apparatus if the anchoring mechanism is manufactured with reusable materials and components.

Within the anchoring mechanism 92 mechanical assembly, traction roller 93 is capable of limited lateral translation (perpendicular to its centerline) in a plane substantially parallel to base platform 921. Lateral translation of the traction roller 93 is limited by the pinch roller 934, the retention pin 928, and traction surface 923. Within these limits the traction roller 93 is free to rotate about its centerline, unless it is engaged with suture line 23 and anchoring mechanism 92 assumes its fully deployed configuration. Axial translation of traction roller 93 (along its centerline) is limited by the base platform 921 and top plate 924 Top plate 924 extends sufficiently over the faces of traction roller 93 to prevent it from exiting the fully assembled anchoring mechanism 92, while still allowing the insertion of retention pin 928 and shoulder bolt 932 into base platform 921. The location of pinch roller 934 on base platform 921, relative to slit-like channel 72, is such that a suture line 23 inserted in said channel 72 and pulled taut laterally outward through the anchoring mechanism 92 and parallel to said channel 72 would contact pinch roller 93 in a substantially tangent orientation. Substantially planar base platform 921 is preferably parallel to the top surface of arcuate rail 71, and preferably offset to a depth at least below the maximum depth of slit-like channel 72, so that a suture line 23 engaged in anchoring mechanism 92 is capable of assuming the deepest position within slit-like channel 72 to tend to minimize its obstruction in arcuate passage 71.

In broad terms, the method of deployment for this third embodiment according to the present invention, consists of:

a) piercing the internal body tissue IBT with needle 20 and threading a length AC of suture line 23 through said internal body tissue IBT;

b) simultaneously inserting both lengths AC and DF of suture line 23 firstly in slit-like channel 72 and secondly in between pinch roller 934 and traction roller 93;

c) grasping both lengths AC and DF of suture line 23, in the vicinity of point A and point F, and retracting pierced internal body tissue IBT by pulling simultaneously both said lengths longitudinally outward through slit-like channel 72 while all the time maintaining suture-line lengths in contact with pinch roller 934 by laterally loading said suture lines against said pinch roller during the said pulling action;

d) once the desired internal body tissue IBT retraction or internal body tissue IBT displacement is obtained, displace the grasped suture lines 23 laterally away from pinch roller 934 towards traction roller 93, such that at least a segment of suture line 23 between point A and point B and at least a segment of suture line 23 between point E and point F engages and exerts a force towards the center of traction roller 93, thereby bringing traction surface 931 into contact with traction surface 923 by virtue of the lateral translation of traction roller 93;

e) while maintaining both lengths of suture line 23 laterally forced against traction roller 93, gradually and slightly reduce the retraction force on the grasped lengths of suture line 23, causing both said lengths to be slightly retrieved longitudinally inward through slit-like channel 72 and entraining traction roller 93 to roll on traction surface 923 towards pinch roller 934;

f) simultaneously releasing grasped lengths AC and DF of suture line 23 when traction roller 93 is only separated from pinch roller 934 by the width of suture line 23 trapped between said rollers at point B and point E of suture line 23.

During step (c) of the method of deployment described above, the lateral loading of suture lines 23 against pinch roller 934 generates a force radially inward towards the centerline of pinch roller 934, which entrains a rotation of pinch roller 934 about its centerline if the friction between contacting suture line 23 and the outer diameter of pinch roller 934 is sufficient to overcome the friction between pinch roller 934 and shoulder bolt 932.

During step (d) of the method of deployment described above, the resultant friction force between suture line 23 and traction ridges 931 when suture lines are laterally forced against traction roller 93, entrains said traction roller to roll towards pinch roller 934, by virtue of the engagement or substantial meshing between ridges 931 and traction surface 923. Once the grasped lengths AC and DF of suture line 23 are released, with suture line pinched between traction roller 93 and pinch roller 934, the friction between traction roller surface 931 and suture line 23, along with the tensile load applied on suture lines 23 from the resistance of the internal body tissue IBT to imposed retraction, will try to entrain traction roller 93 to roll even closer to pinch roller 934 by virtue of its continued engagement with traction surface 923, and thereby tend to increase the pinching load on suture line 23 between traction roller 93 and pinch roller 934.

Disengagement is accomplished by grasping the lengths AC and DF of suture line 23 in the vicinity of point A and point F, and simultaneously pulling on said lengths to increase the retraction load on the internal body tissue IBT beyond the load currently delivered through the traditional suture 13 being engaged in the fully deployed anchoring mechanism 92. This action relieves the internal body tissue IBT retraction force from the surgical apparatus back to the surgeon's hand, and entrains traction roller to roll away from pinch roller thereby releasing the pinching or wedging effect between 931 and 934 responsible for securing or fixing suture line relative to the anchoring mechanism. Readjustment of the magnitude of internal body tissue IBT retraction or internal body tissue IBT displacement may at this point be accomplished by repeating steps (c) to (f) above. Readjustment for the direction of the applied internal body tissue IBT retraction load or for the direction of exerted displacement on the internal body tissue IBT may be accomplished by disengaging the suture line 23 in manner described above, and repeating steps (c) to (f) above but engaging anchoring mechanism 92 located in another position on sternum retractor 1.

To facilitate the insertion of suture line 23 between the pinch roller 934 and the traction roller 93, the pinch roller 934 is configured with a dome shaped shoulder 935 and the traction roller 93 is configured with a beveled edge 938. Alternatively, the height of pinch roller 934 or shoulder bolt 932 may extend above the plane of top plate 924 to facilitate insertion of suture line 23 between said pinch and traction rollers. In both cases, height of pinch roller 934 is preferably at least equal to the height of traction roller 93.

The traction ridges 931 on the traction roller 93 are preferably substantially V-shaped longitudinal ridges, and the traction surface 923 on wall 925 is preferably configured with longitudinal substantially V-shaped grooves extending from the base platform 921 to the top plate 924 of housing 922. A variety of other cooperating surface textures or cooperating surface profiles configured on the cylindrical surface of traction roller 93 and the textured portion of wall 925, may also be used to provide a substantial meshing between said components or substantially slip free rolling of traction roller 93 on traction surface 923 when said roller is loaded against said traction surface during the deployment of tissue retractor 13, in manner described above.

Figure 7A:
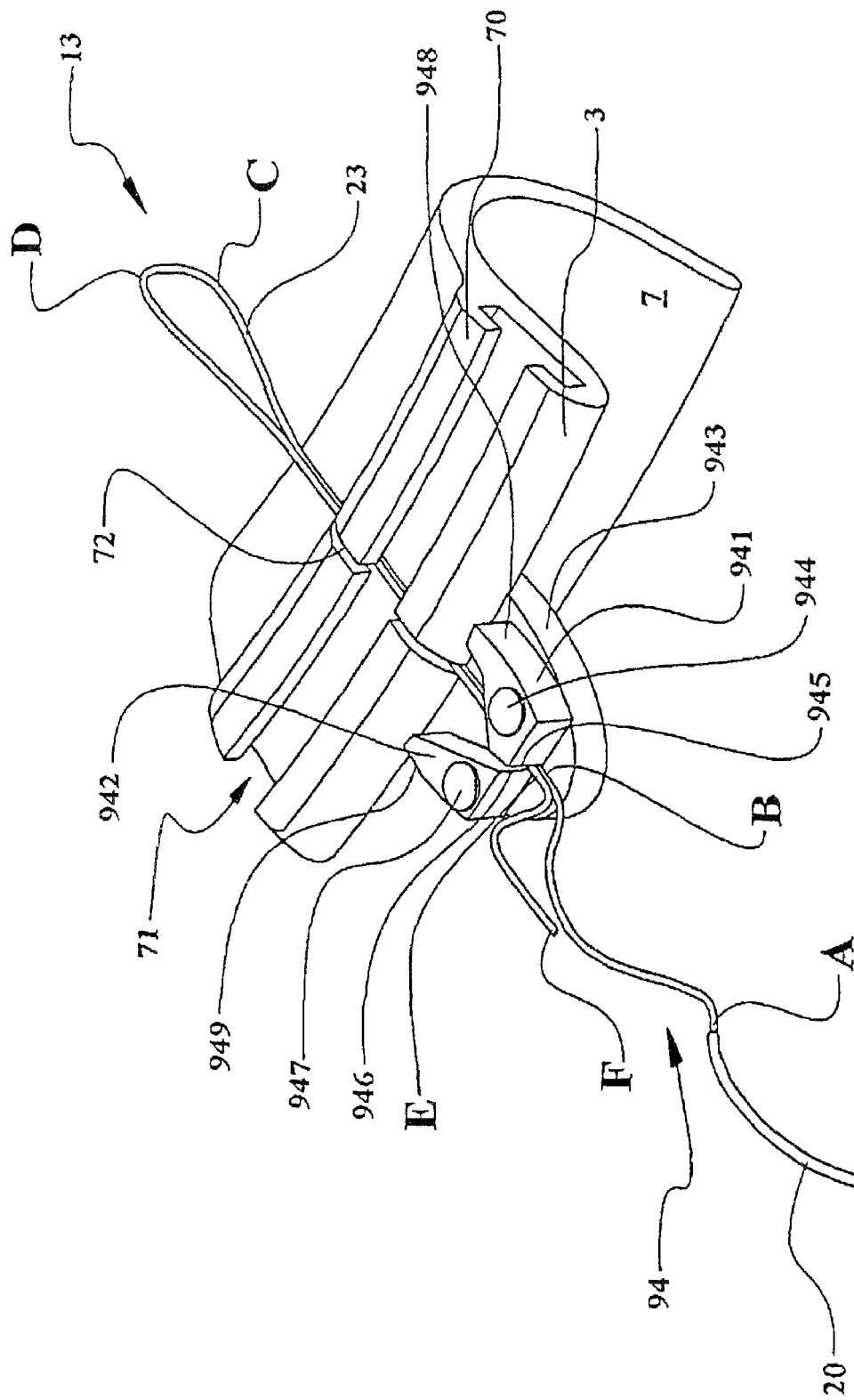
FIG. 7A is a perspective view of a tissue retractor comprising a suture and associated anchoring mechanism according to a fourth embodiment of the present invention.
Figure 7B:
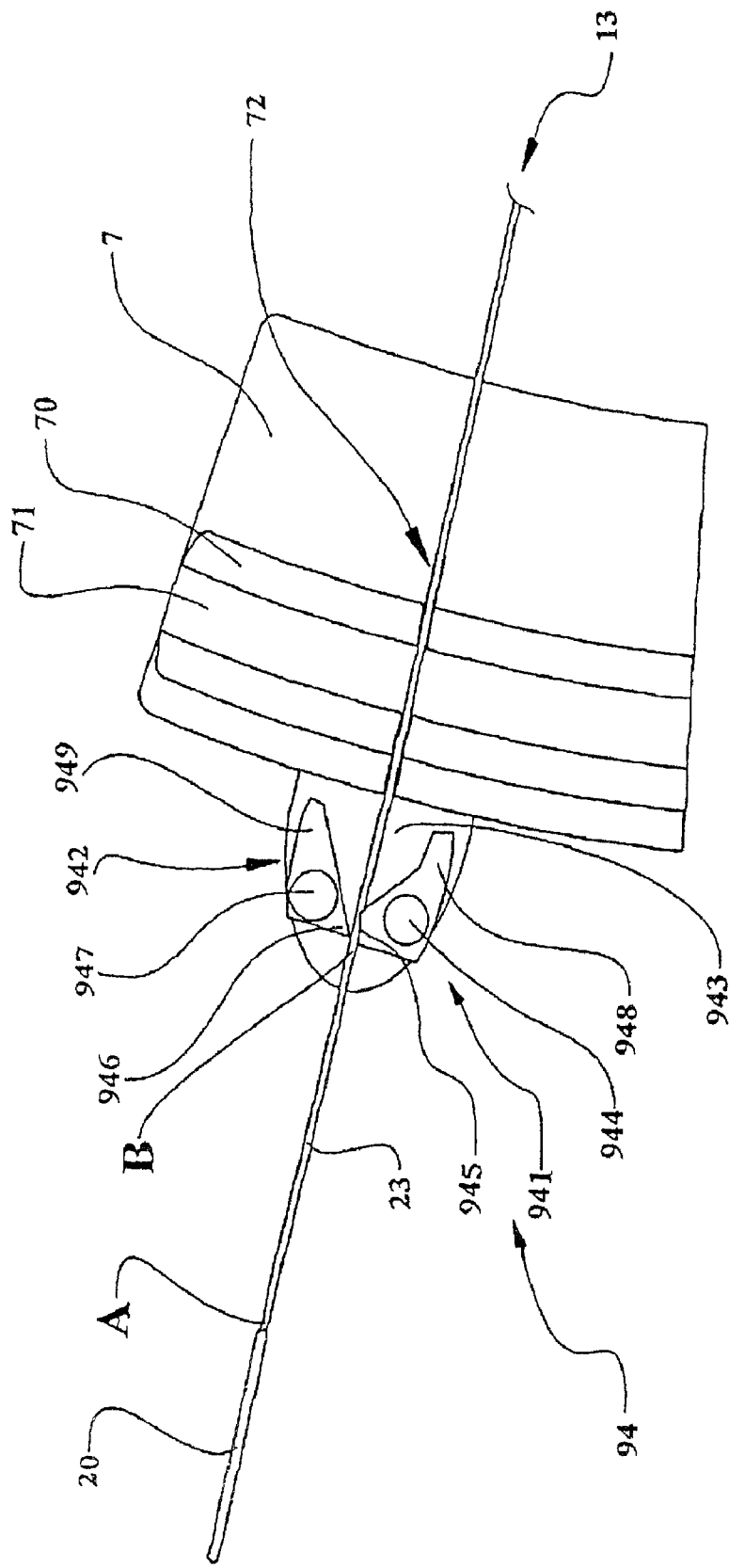
FIG. 7B is a top view of the tissue suture and associated anchoring mechanism of FIG. 7A comprising a pawl-shaped lever member.

FIGS. 7A-7B illustrate a fourth embodiment according to the present invention. Internal body tissue IBT retraction will be effectuated with a traditional suture 13, comprised of a curved suture needle 20 and a suture line 23, that becomes engaged with anchoring mechanism 94 disposed on sternum retractor 1, in a plurality of locations similar to the disposition of anchoring ports 90 of the first embodiment. FIG. 7A illustrates only the most remote portion relative to rack bar 5 of retractor spreader arm 3, with one anchoring mechanism 94 disposed laterally outward on said arm 3.

Anchoring mechanism 94 is comprised of a fitting 943, and two pawl-shaped levers: an anvil-like pawl 941 and a wedge-like pawl 942. Fitting 943 may be either an integral extension of retractor arm 3 (or 4) or may be mechanically fastened to said retractor arm to form a rigid assembly during at least the duration of the surgical intervention requiring tissue retraction. Fitting 943 is preferably disposed below the depth of slit-like channel 72. Anvil-like pawl 941 and wedge-like pawl 942 are preferably rotatingly engaged with fitting 943 by pivot pins 944 and 947, respectively, which are inserted through cylindrical bores in said pawls (not shown). Pivot pins 944 and 947 are rigidly mounted to fitting 943 through a variety of ways, such as: a threaded interface, by riveting, by brazing, or other like ways, in order to keep the components comprising the anchoring mechanism 94 as an integral mechanical assembly. The centerlines of the pivot pins 944 and 947 are parallel to each other. Anvil-like pawl 941 is configured with a jaw 945 which comprises a planar face portion, and wedge-like pawl 942 is configured with a jaw 946 which comprises a sharp wedge, said jaws cooperating together and capable of providing a concentrated clamping load to a suture line 23 which becomes engaged between said jaws, as illustrated in FIG. 7B. Also disposed between pivot pin 944 and cylindrical bore of anvil-like pawl 941 is a torsion spring (not shown), engaging between pawl 941 and pivot pin 944, or alternatively between pawl 941 and fitting 943. Similarly, disposed between pivot pin 947 and cylindrical bore of wedge-like pawl 942 is another torsion spring, engaging between pawl 942 and pivot pin 947, or alternatively between pawl 942 and fitting 943. The said torsion springs serve to rotate pawls 941 and 942, in opposing directions, until their respective jaws 945 and 946 come and remain in contact. The angular rotation of at least one of the pawls 941 or 942, about its respective pivot pin 944 or 947, preferably anvil-like pawl 941, is contained within a range of angular positions thereby ensuring that the sharp wedge portion of jaw 946 will only contact the flat face portion of cooperating jaw 945 (when the suture is not engaged) by the action of the said torsion springs. The angular rotation of at least one of the pawls 941 or 942 may be contained within the desired range of angular positions by limit stops or limit pins (not shown), for example, disposed on the top face of fitting 943 and capable of contacting at least a portion of the affected pawl at the limit position of the said range of angular positions. Alternatively, an external circumferential notch on pivot pin 944 or 947, that is contacted by a narrower protrusion on pawl 941 or 942 respectively that extends into the cylindrical bore of said pawl 941 or 942, may serve to limit the desired angular range of position for the affected pawl.

By virtue of said torsion springs, jaws 945 and 946 are capable of applying a spring-induced clamping force to a suture line 23 which becomes inserted between said jaws. The magnitude of this spring-induced clamping force may be increased by increasing the spring stiffness of said torsion springs. The topmost portion of jaws 945 and 946 may be chamfered or profiled (not shown) to facilitate insertion of suture line 23 between spring loaded pawls 941 and 942.

In broad terms, the method of deployment for this fourth embodiment according to the present invention, consists of:

a) piercing the internal body tissue IBT with needle 20 and threading a length AC of suture line 23 through said internal body tissue IBT;

b) simultaneously inserting both lengths AC and DF of suture line 23 firstly in slit-like channel 72 and secondly in between jaw 945 of anvil-like pawl 941 and jaw 956 of wedge-like pawl 942;

c) rasping both lengths AC and DF of suture line 23, in the vicinity of point A and point F, and retracting pierced internal body tissue IBT by pulling simultaneously both said lengths longitudinally outward through slit-like channel 72 and through jaws 945 and 946, sufficiently to obtain the desired internal body tissue IBT retraction or displacement;

d) simultaneously releasing both lengths AC and DF of suture line 23, jaws 945 and 946 being in contact with the suture line 23 at point B and point E of said suture line;

e) if required, readjusting to increase the magnitude of internal body tissue IBT retraction or displacement, by simultaneously grasping suture line 23 between lengths AB and EF, and pulling simultaneously both said lengths in manner described in step (c) above;

f) if required, readjusting to decrease the magnitude of internal body tissue IBT retraction or displacement, by: (i) simultaneously grasping suture line 23 between lengths AB and EF, and pulling simultaneously both said lengths upward away from fitting 943, in a pulling direction substantially parallel to centerline of pivot pins 944 and 947, to disengage suture line 23 from contact with jaws 945 and 946 of pawls 941 and 942, respectively, (ii) relieving internal body tissue IBT retraction load by applying no pulling force on said grasped suture line 23, (iii) re-engaging suture line 23 with jaws 945 and 946 to secure desired internal body tissue IBT retraction or displacement by repeating steps (c) and (d) described above;

g) if required, readjusting the direction of retraction load applied to internal body tissue IBT or readjusting the direction of displacement exerted on internal body tissue IBT by disengaging suture line 23 from existing anchoring mechanism 94 and re-engaging suture line 23 in another anchoring mechanism 94 disposed in an alternate location on sternum retractor 1, by repeating steps (c) to (f) described above.

Alternatively, steps (b) and (c) of the method of deployment described above may be reversed by first pulling simultaneously and sufficiently both lengths AC and DF longitudinally outward from surgical window SW to obtain the desired internal body tissue IBT retraction or displacement, and subsequently inserting simultaneously both said lengths of suture line 23 firstly in slit-like channel 72 and secondly in between jaws 945 and jaw 946 of anchoring mechanism 94.

During step (b) of the first method of deployment described above, a spring-induced clamping force is applied to the portions of suture line 23 inserted between jaws 945 and 946, by virtue of the torsion spring acting between pawl 941 and pivot pin 944 and the torsion spring acting between pawl 942 and pivot pin 947. There is no tension in suture line 23 since the internal body tissue IBT is not yet retracted. In the alternate method of deployment, only the spring-induced clamping force acts on the portions of suture line 23 inserted between jaws 945 and 946 as long as the tension in lengths AC and DF of suture line 23 resulting from the imposed retraction on internal body tissue IBT, or from the displacement exerted on internal body tissue IBT, is reacted by the surgeon's hand and not the anchoring mechanism 94.

During step (d) of the first method of deployment described above, the resulting tension in lengths AC and DF of suture line 23 from the imposed retraction on internal body tissue IBT, or from the displacement exerted on the internal body tissue IBT, is reacted by anchoring mechanism 94. When tension is applied to the suture line 23 simultaneously at point C and point D by the retracted internal body tissue IBT, the friction force between the suture line 23 (at points B and E) and each of jaws 945 and 946 will cause the pawls 941 and 942 to rotate in opposition, beyond the point of rotation of said pawls when only the action of the torsion springs places said jaws of said pawls in contact with the portion of inserted suture line 23. Consequently, the normal force on the suture line 23 at point B and point E will be increased beyond the spring-induced clamping force. The distance between the axis of pivot pin 947 and jaw 946 is only slightly larger than half the distance between the axis of pivot pin 944 and the axis of pivot pin 947, and similarly the distance between the axis of pivot pin 944 and jaw 945 is only slightly larger than half the distance between the axis of pivot pin 944 and the axis of pivot pin 947 such that the increase in normal force on point B and point E of suture line 23 caused by tension applied to the said suture line simultaneously at point C and point D will always result in a clamping friction force which is greater than the tension applied to the suture line 23, where the said clamping friction force is equivalent to the normal force on the suture line 23 at point B and point E multiplied by the coefficient of friction between each of the said jaws and the suture line 23 at point B and point E. With the said clamping friction force greater than the tension on the suture line 23, the suture line 23 is fully engaged in anchoring mechanism 94, and the suture line 23 should not slip through the jaws 945 and 946 of pawls 941 and 942 thereby securing the desired internal body tissue IBT retraction or internal body tissue IBT displacement.

The disengagement of suture line 23 according to step (f) in above description of the method of deployment may be facilitated by applying a compression force between extension 948 and extension 949 of pawls 941 and 942, respectively. This compression force causes pawls 941 and 942 to rotate in opposition thereby releasing portion of suture line 23 inserted or engaged between their respective jaws 945 and 946.

In this fourth embodiment as illustrated in FIGS. 7A-7B, the line of contact that results between jaw 945 which comprises a planar face portion and jaw 946 which comprises a sharp wedge portion, when said jaws come into contact by the rotation of pawls 941 and 942 about their respective pivot pin 944 and 947, is preferably parallel to the centerline of said pivot pins. As illustrated, the line of contact is preferably configured over the entire height of jaws 945 and 946, but may also be reduced provided at least a portion remains available for engagement of suture line 23 between said jaws.

Other variants for the line of contact are also possible without departing from the spirit of this embodiment of the present invention. For example, a grooved recess may be configured across the planar face portion of jaw 945 (said grooved recess substantially perpendicular to the centerline of pivot pin 944) serving to locate a portion of suture line 23 therein. The cooperating sharp wedge portion of jaw 946 will be configured with a protruding wedge profile that conforms to grooved recess profile, such that the distance between the axis of pivot pin 947 and protruding wedge profile of jaw 946 is only slightly larger than half the distance between the axis of pivot pin 944 and the axis of pivot pin 947, and similarly the distance between the axis of pivot pin 944 and grooved recess of jaw 945 is only slightly larger than half the distance between the axis of pivot pin 944 and the axis of pivot pin 947.

Alternatively, without departing from the spirit of this fourth embodiment, those skilled in this act will appreciate that pawls 941 and 942 may provide opposed cam-like surfaces which serve as engaging jaws for the suture line. Alternatively, without departing from the spirit of this fourth embodiment, one of the pawls 941 or 942, preferably anvil-like pawl 941 may be rigidly fixed relative to the fitting 943 and thereby act as a rigid engagement surface for cooperation with wedge-like pawl 942 which is rotatingly engaged to fitting 943 as previously described.

FIGS. 7A-7B illustrate a reusable anchoring mechanism 94, integral with sternum retractor 1. Alternatively, a disposable anchoring mechanism 94 assembly may be designed and mechanically attached to a reusable sternum retractor 1 and replaced after every surgical intervention. Alternatively, if a disposable sternum retractor 1 is designed, the members comprising anchoring mechanism 94 may also be disposable and fabricated in single-use plastic or polymeric materials, for instance.

An alternate design and configuration for incorporating anchoring mechanism 94 with sternum retractor 1 consists of embedding said anchoring mechanism within arcuate arm 3 (or 4) below the surfaces defining arcuate passage 71, and deepening slit-like channel 72 accordingly. As a result, the positioning and articulation mechanism previously described may be inserted in arcuate passage 71, positioned along arcuate passage 71, and engaged with arcuate rail 70 even in a position over the location of embedded anchoring mechanism 94, without any resulting obstruction to said positioning and articulation mechanism from a suture line secured relative to anchoring mechanism 94.

Figure 8A:
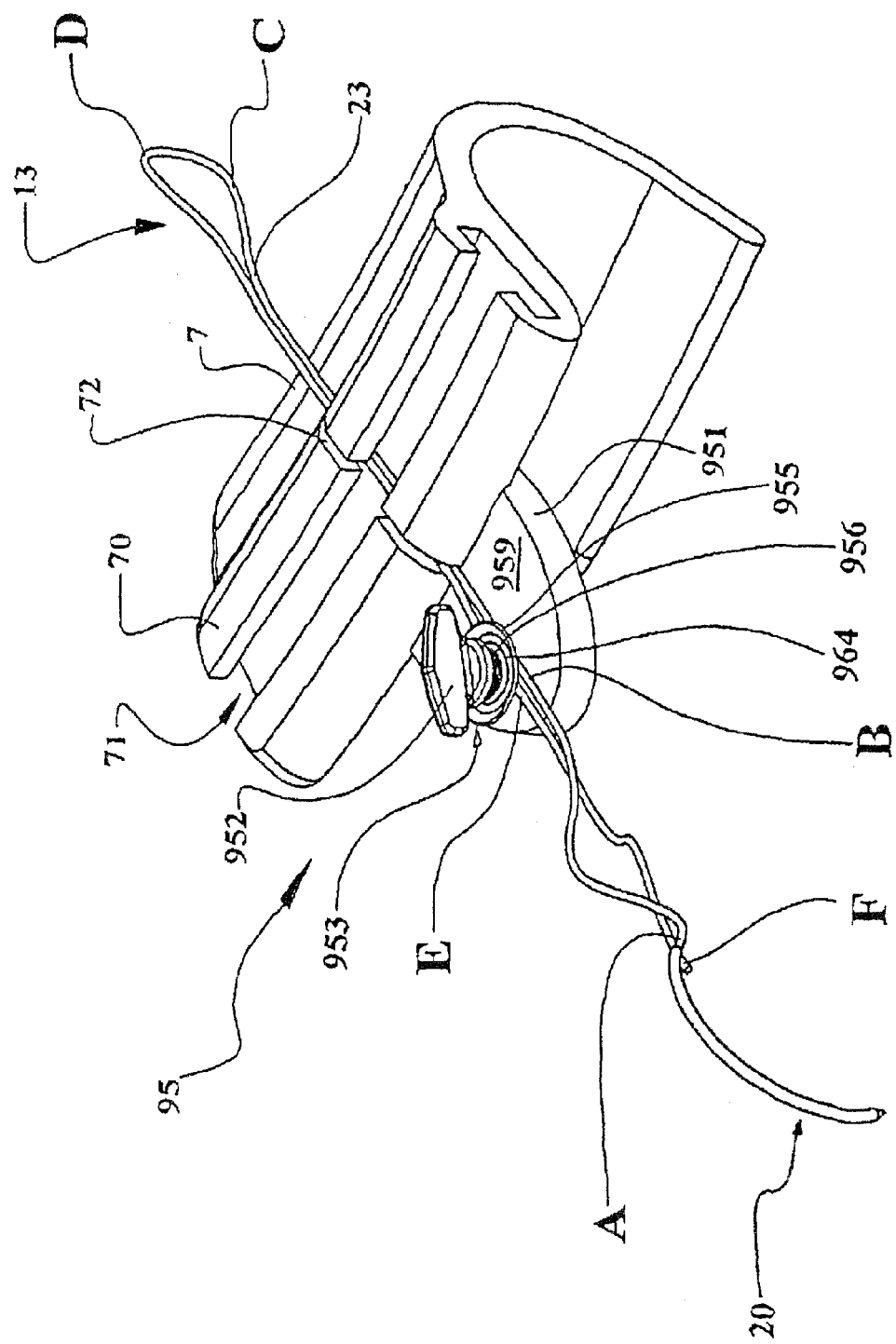
FIG. 8A is a perspective view of a tissue retractor comprising a suture and associated anchoring mechanism according to a fifth embodiment of the present invention.
Figure 8B:
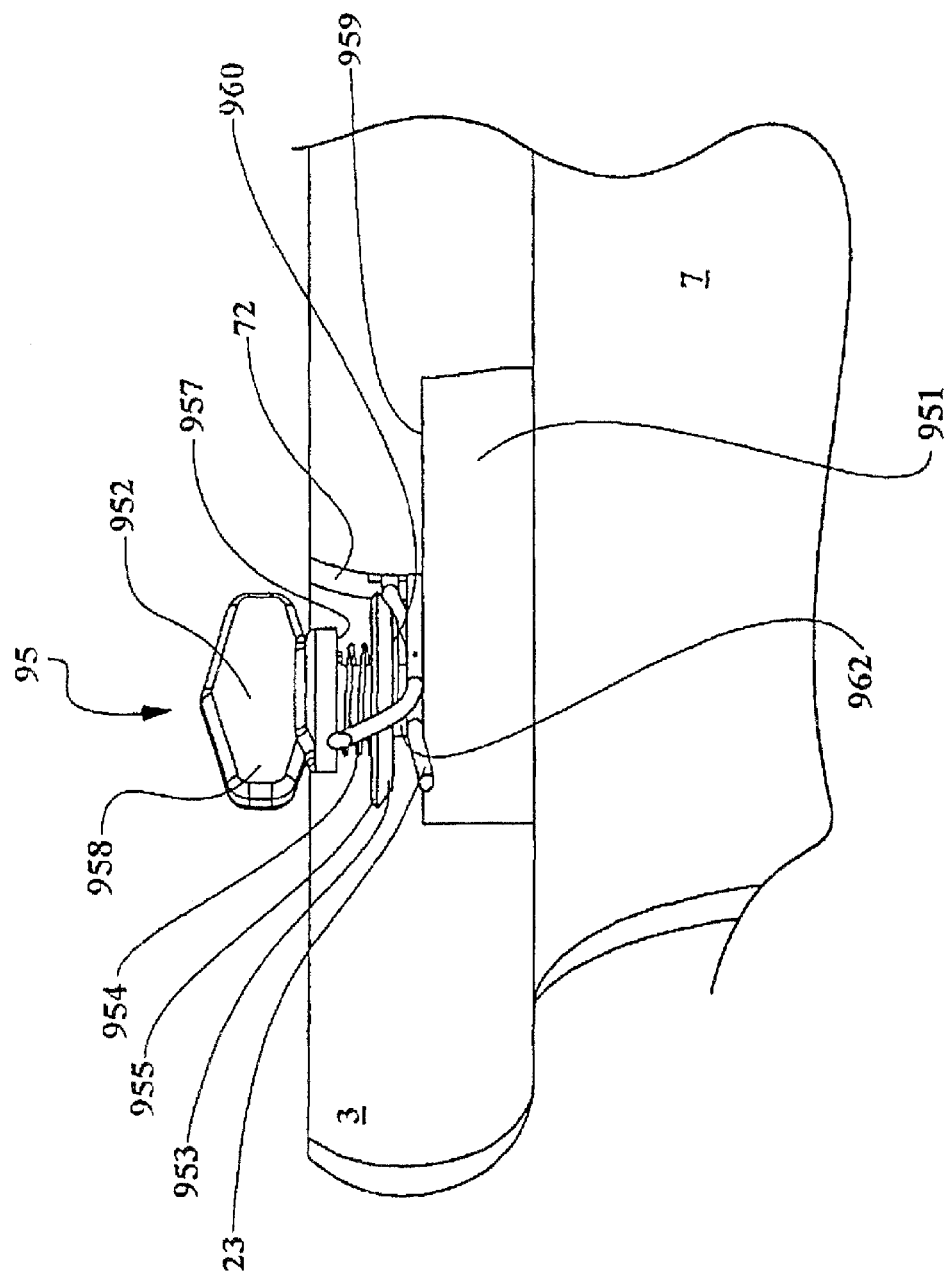
FIG. 8B is a side elevational view of the suture and associated anchoring mechanism of FIG. 8A comprising a screw member and spring-loaded washer member.

FIGS. 8A-8B illustrate a fifth embodiment according to the present invention, one that allows the possibility of adjusting the magnitude of the clamping load on suture line 23. Internal body tissue IBT retraction will be effectuated with a traditional suture 13, comprised of a curved suture needle 20 and a suture line 23, that becomes engaged with anchoring mechanism 95 disposed on sternum retractor 1, in a plurality of locations similar to the disposition of anchoring ports 90 of the first embodiment. FIG. 8A illustrates only the most remote portion relative to rack bar 5 of retractor spreader arm 3, with one anchoring mechanism 95 disposed laterally outward on said arm 3.

Anchoring mechanism 95 is comprised of a fitting 951, a profiled washer 953, a helical spring 954, and a screw 952. Fitting 951 may be either an integral extension of retractor arm 3 (or 4) or may be mechanically fastened to said retractor arm to form a rigid assembly during at least the duration of the surgical intervention requiring tissue retraction. Fitting 951 is preferably disposed below the depth of slit-like channel 72. Screw 952 is comprised of a knob 958, a shoulder 957, and a threaded shaft 962. Helical spring 954 is first inserted over threaded shaft 962, placed in contact with the shoulder 957 of screw 952, said shoulder having a diameter greater than diameter of helical spring 954, and preferably a groove on face of said shoulder to house first winding of said helical spring. Profiled washer 953 is next inserted over threaded shaft 962. Screw 952 is then engaged with fitting 951, by virtue of threaded shaft 962 inserted into fitting threaded hole (not shown), in order to configure the mechanical assembly of components defining the anchoring mechanism 95. The fitting threaded hole is preferably a through hole, such that screw 952 may be threaded sufficiently into threaded fitting hole to extend below fitting 951. The exposed portion of threaded shaft 962 may, at this point, be: (i) mechanically flared outwards, or (ii) engaged with a transverse retention pin fitted through a hole in said threaded shaft, or (iii) engaged with a circular clip fitted into an annular groove in said threaded shaft, or (iv) engaged with a nut threaded member threaded on extreme-most portion of said threaded shaft, or (v) be engaged with other similar mechanical member preventing said threaded shaft from being withdraw from said fitting threaded hole without first disengaging mechanical member. This prevents inadvertent disassembly of the anchoring mechanism 95 during the surgical intervention, that may result by sufficiently unthreading and disengaging threaded shaft 962 from fitting threaded hole. Profiled washer 953 is designed with both its outer perimeter 955 and inner perimeter 956 bent significantly away from bottom face 960 of profiled washer 953 to create firstly, a socket 964 on the top face of profiled washer 953 to locate helical spring 954 and secondly, a beveled outside edge between outer perimeter 955 and bottom face 960 of said profiled washer serving as a guide to facilitate the insertion of suture line 23 between said bottom face 960 and top face 959 of fitting 951.

When anchoring mechanism 95 is mechanically assembled, the helical spring 954 is axially trapped between shoulder 957 of screw 952 and socket 964 of profiled washer 953, but also free to rotate about its centerline. Helical spring 954 is also free to rotate relative to screw 952 and free to rotate relative to washer 953. Turning knob 958 of screw 952 such that it decreases the distance between shoulder 957 and fitting face 959 will increase the mechanical force that helical spring 954 applies on profiled washer 953. Conversely, if knob 958 is unscrewed sufficiently, the increase in distance between shoulder 957 and fitting face 959 will unload the helical spring 954 entirely, and rendering the insertion of the portion of suture line 23 between face 960 of profiled washer 953 and face 959 of fitting 951. To increase the clamping load on the portion of suture line 23 between said faces 959 and 960, knob 958 is turned until the load applied by the helical spring 954 on profiled washer 953 is sufficiently great to prevent suture line 23 from slipping out between said faces 959 and 960 given a specific internal body tissue IBT retraction load.

In broad terms, the method of deployment for this fifth embodiment according to the present invention, consists of:

a) piercing the internal body tissue IBT with needle 20 and threading a length AC of suture line 23 through said internal body tissue IBT;

b) simultaneously inserting both lengths AC and DF of suture line 23 firstly in slit-like channel 72 and secondly in between bottom face 960 of profiled washer 953 and face 959 of fitting 951;

c) grasping both lengths AC and DF of suture line 23, in the vicinity of point A and point F thereof, and retracting pierced internal body tissue IBT by pulling simultaneously both said lengths longitudinally outward through slit-like channel 72 and through in between face 960 and face 959, sufficiently to obtain the desired internal body tissue IBT retraction or displacement;

d) screwing knob 958 sufficiently such that the clamping load on profiled washer 953, and consequently on the suture line 23 at point B and point E, is sufficient to react the required retraction load for desired internal body tissue IBT retraction or displacement;

e) simultaneously releasing both lengths AC and DF of suture line 23, profiled washer 953 being in contact with the suture line 23 at point B and point E of said suture line;

f) if required, readjusting the magnitude of internal body tissue IBT retraction or displacement, by simultaneously grasping suture line 23 between lengths AB and EF, unscrewing knob 958 and pulling simultaneously both said lengths in manner described in step (c) above;

g) if required, readjusting the direction of retraction load applied to the internal body tissue IBT or readjusting the direction of displacement exerted on the internal body tissue IBT by disengaging suture line 23 from existing anchoring mechanism 95, and re-engaging suture line 23 in another anchoring mechanism 95 disposed in an alternate location on sternum retractor 1, by repeating steps (c) to (e) described above.

This fifth embodiment offers advantages in that the clamping load on traditional suture 13 may be tailored to a specific surgical intervention, or to the specific internal body tissue that will be retracted or displaced. For example, if the risk of applying an exceedingly high load during a surgical intervention on the retracted internal body tissue IBT will result in unwanted tearing of body tissue, the maximum clamping load that can be exerted on the suture line 23 may be set to a prescribed value by turning knob 958 a specific amount that will preload helical spring 954 such that surgical loads applied to the internal body tissue IBT higher than this prescribed value will result in the suture line 23 being released from anchoring mechanism 95, rather than resulting in unwanted tearing of body tissue or unwanted tissue trauma. In this manner, the components of the anchoring mechanism 95 cooperate to provide a failsafe feature.

FIG. 8B illustrates suture line 23 inserted in anchoring mechanism 95, during step (b) of the method of deployment described above, with screw 952 sufficiently unscrewed to relieve profiled washer 953 and portion of suture line 23 inserted in anchoring mechanism 95 free of any clamping load from helical spring 954.

If it is desired to ensure that profiled washer 953 will not rotate relative to screw 952 when turning knob 958, a guide pin (not shown) may be inserted into top face 959 of fitting 951, said pin standing sufficiently proud above said surface 959 that it is capable of engaging a hole, eccentrically located relative to the centerline of profiled washer 953, thereby fixing the angular rotational position of profiled washer 953 relative to fitting 951.

Alternatively, this fifth embodiment may be modified to provide clamping of a portion of suture line 23 without the failsafe feature described above, and without a controllable application of clamping load on said portion of suture line. Spring 954 and profiled washer 953 may be eliminated and the portion of suture line 23 clamped between shoulder 957 of screw 952 and face 959 of fitting 951. As a result, only two substantially discrete clamping load settings are obtained, either zero clamping or fully-engaged-thread clamping load for a specific thread 962 size. Alternatively, other variants to this fifth embodiment are possible such as those which may incorporate a Belleville washer, wave spring, helical spring washer, or other like washers, known in the field of mechanical design and available in a variety of sizes and shapes.

Figure 9A:
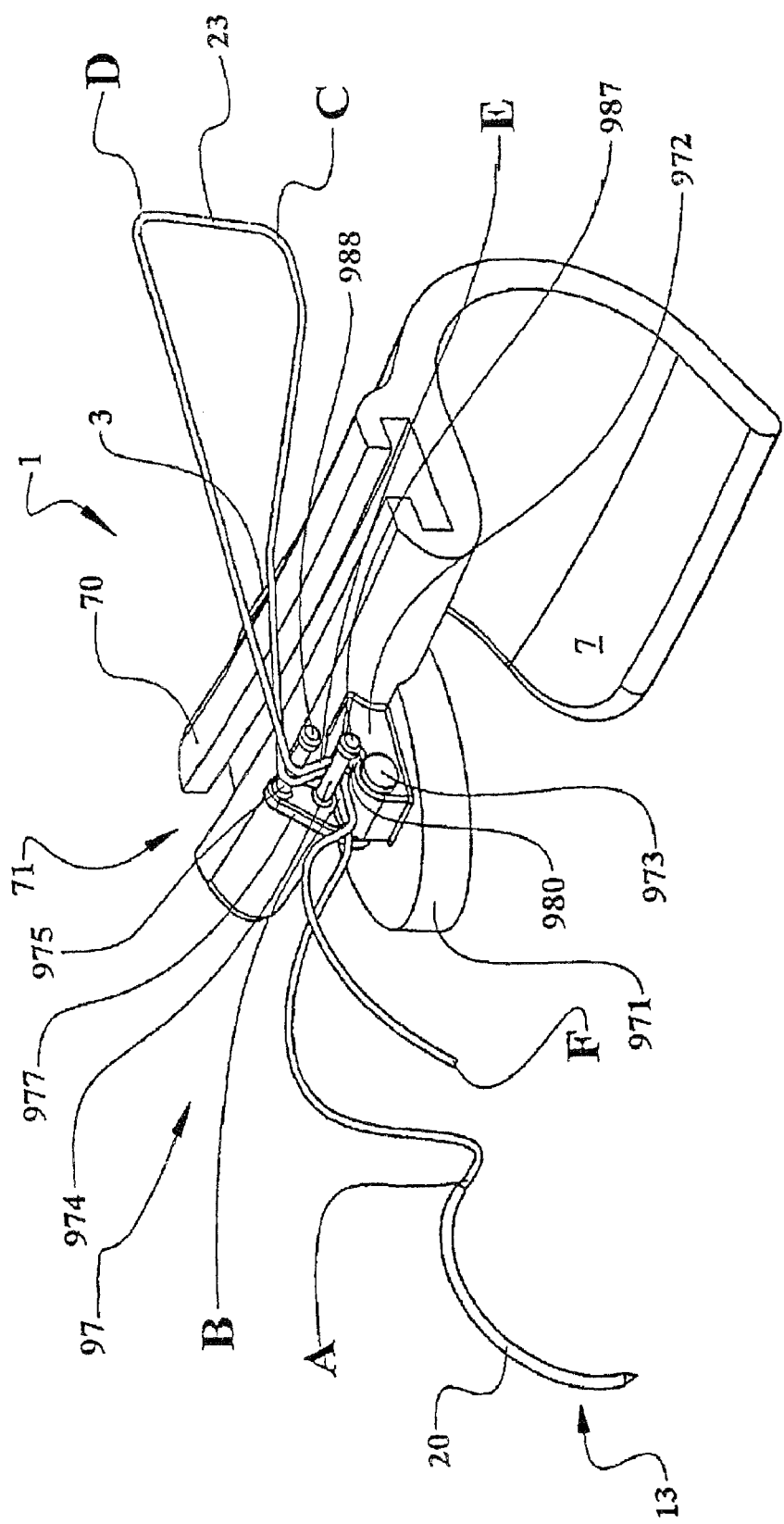
FIG. 9A is a perspective view of a tissue retractor comprising a suture and associated anchoring mechanism according to a sixth embodiment of the present invention.
Figure 9B:
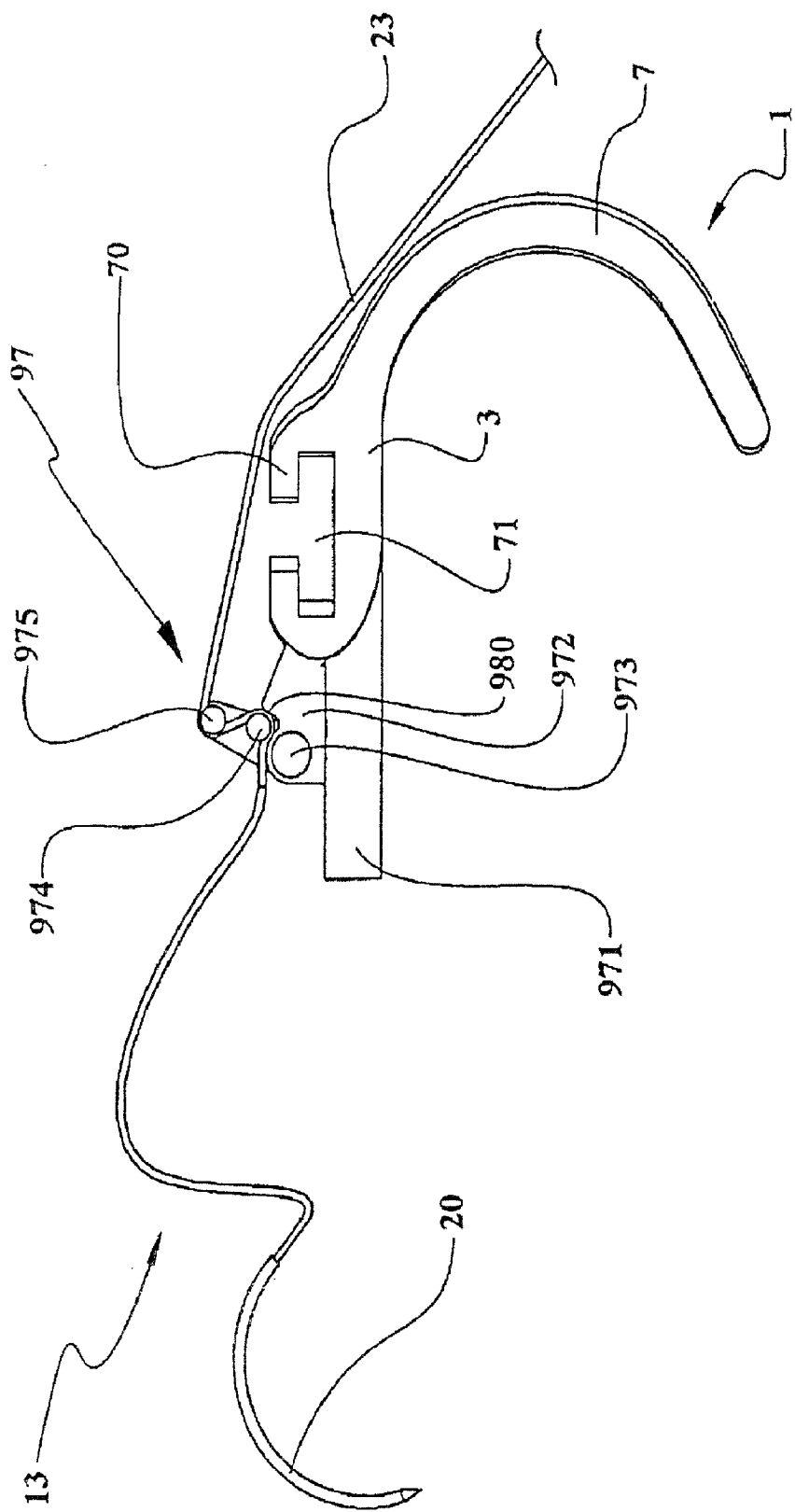
FIG. 9B is a side elevational view of the suture and associated anchoring mechanism of FIG. 9A comprising a swing plate lever member.

FIGS. 9A-9B illustrate a sixth embodiment according to the present invention, one that tends to be energized by the very tension it is intended to react in suture line of tissue retractor. Internal body tissue IBT retraction will be effectuated with a traditional suture 13, comprised of a curved suture needle 20 and a suture line 23, that becomes engaged with anchoring mechanism 97 disposed on sternum retractor 1, in a plurality of locations similar to the disposition of anchoring ports 90 of the first embodiment. FIG. 9A illustrates only the most remote portion relative to rack bar 5 of retractor spreader arm 3, with one anchoring mechanism 97 disposed laterally outward on said arm 3.

Anchoring mechanism 97 is comprised of a fitting 971, a carriage 972, a swing plate 977, a pinch arm 974, and an energizing arm 975. Fitting 971 may be either an integral extension of retractor arm 3 (or 4) or may be mechanically fastened to said retractor arm to form a rigid assembly during at least the duration of the surgical intervention requiring tissue retraction.

Swing plate 977 is rotatingly engaged with carriage 972 by pivot pin 973, which is firstly slidingly inserted through a cylindrical bore (not shown) in carriage 972, and secondly rigidly engaged into an opening on swing plate 977, by a variety of ways similar to the rigid engagement of pins in previously described embodiments. Swing plate 977 is free to rotate about the centerline axis of pivot pin 973, which axially retains said swing plate 977 relative to carriage 972. Swing plate 977 is comprised of two substantially cylindrical cantilevered shafts, a pinch arm 974 and an energizing arm 975, both of which are preferably rigidly attached to swing plate 977, and both of which have their longitudinal axes preferably perpendicular to plate 977. Pinch arm 974 is positioned on plate 977 such that substantially cylindrical surface 979 of pinch arm 974 opposes carriage surface 980 when said swing plate 977 rotates to clamp across a portion of suture line 23 inserted and engaged between said surfaces 979 and 980. The axis of pivot pin 973, longitudinal axis of pinch arm 974, the longitudinal axis of energizing arm 975, and the longitudinal axis of carriage surface 980 are all parallel to each other.

In broad terms, the method of deployment for this sixth embodiment according to the present invention, consists of:

a) piercing the internal body tissue IBT with needle 20 and threading a length AC of suture line 23 through said internal body tissue IBT;

b) simultaneously inserting both lengths AC and DF of suture line 23 between energizing arm 975 and pinch arm 974 by winding said both lengths firstly around the energizing arm 975 and secondly around the pinch arm 974 as illustrated in FIG. 7A;

c) grasping both lengths AC and DF of suture line 23, in the vicinity of point A and point F, and retracting pierced internal body tissue IBT by pulling simultaneously both said lengths longitudinally outward through anchoring mechanism 97 (in direction perpendicular to axis of pivot pin 973), sufficiently to obtain the desired internal body tissue IBT retraction or displacement;

d) simultaneously releasing both lengths AC and DF of suture line 23, resulting in point B and point E of said suture line being engaged between cylindrical surface 979 and carriage surface 980;

e) if required, readjusting the magnitude of internal body tissue IBT retraction or displacement, by simultaneously grasping both lengths AB and EF of suture line 23, and pulling simultaneously both said lengths in manner described in step (d) above;

f) if required, readjusting the direction of retraction load applied to internal body tissue IBT or readjusting the direction of displacement exerted on the internal body tissue IBT by disengaging suture line 23 from existing anchoring mechanism 97, and re-engaging suture line 23 in another anchoring mechanism 97 disposed in an alternate location on sternum retractor 1, by repeating steps (c) to (e) described above.

When a tension load is applied to suture line 23 at point C and D, and when said suture line is in tension and deflected around energizing arm 975 as illustrated in FIG. 7A, the normal force between cylindrical surface 979 and carriage surface 980 is amplified relative to both the tension acting on suture line 23 and the closing force acting on energizing arm 975, by virtue of the leverage effect imparted by swing plate 977. The distance between longitudinal axis of pinch arm 974 to the centerline of pivot pin 973 is inferior to the distance between longitudinal axis of energizing arm 975 to the centerline of pivot pin 973, preferably by 30 to 70 percent, such that the resultant clamping force generated by the amplified normal force between cylindrical surface 979, carriage surface 980, and the portion of suture line 23 engaged therebetween will always be greater than the tension applied in suture line 23 at point C and D. The said resultant clamping force being greater than the said tension results in the suture line 23 being secured relative to anchoring mechanism 97.

Tension applied to suture line 23 at point A and point F opposes and reduces the resultant clamping force on suture line 23 at point B and point E engaged between cylindrical surface 979 and carriage surface 980. Tension applied to suture line 23 at point A and point F can be applied to such an extent as to completely overcome the said resultant clamping force, thus allowing suture line 23 to be pulled, as desired, to slide through the cooperating surfaces 979 and 980 of anchoring mechanism 97 in the direction of application of said tension. Guide knob 987 on pinch arm 974 and guide knob 988 on energizing arm 975 serve to discourage disengagement of suture line 23 from said arms 974 and 975 should there be any significant misalignment between either of length AC or length DF of suture line 23 and a plane perpendicular to the longitudinal axes of arms 974 and 975.

FIG. 9A-9B illustrates this sixth embodiment according to the present invention with the engaged suture line 23 extending above both the arcuate rail 70 and arcuate passage 71. Alternatively, similar to the previous embodiments, the fitting 971 and carriage 972 may be configured at a lower depth on sternum retractor 1, and slit-like passages 72 included in arcuate arm 3 such that the engaged suture line 23 will rest at the maximum depth of slit-like channel 72 thereby providing an unobstructed access to arcuate passage 71 for the positioning and articulation mechanism described above.

The embodiments of the present invention may be used in beating heart coronary artery bypass graft (CABG) surgery to position and orient the beating heart within the retracted chest cavity of the patient by applying a tissue retraction load to the pericardium tissue. The pericardium tissue is typically incised to expose at least a portion of the heart surface where the bypass graft will be performed, but remains anatomically attached to the beating heart. For example, the pericardium tissue may be engaged by a number of tissue retractors secured to either anchoring ports or anchoring mechanisms, according to the present invention, in order to place the longitudinal axis of the of beating heart in a substantially vertical orientation to facilitate grafting of the posterior arteries. A number of tissue retractors comprising a curved needle 20 and a suture line 23 may pierce the pericardium tissue close to the base of the heart (or close to the pericardial reflection): one tissue retractor placed between the superior and inferior pulmonary vein, a second tissue retractor below the inferior pulmonary vein, a third one midway between the apex of the heart and the inferior pulmonary vein, and a fourth one towards the diaphragmatic face near the inferior vena cava. Retraction loads are subsequently applied to these tissue retractors, and said tissue retractors each secured to an anchoring mechanism disposed on sternum retractor 1 thereby maintaining the desired tissue retraction, in one of the manners described above, according to the present invention.

The above descriptions of the preferred embodiments should not be interpreted in any limiting manner since variations and refinements are possible without departing from the spirit of the invention. For example, the tissue-piercing needle 20 may be either solid throughout or of a hollow cross-section, the curvature of the needle may be of any number of variants from almost straight to slightly curved to curved, cross section can be circular or elliptical or have a local flat spot, along the curved length of the needle, to improve the stability of the clamped needle within the mating jaws of a surgical clamp used while piercing tissue or some other manipulation with the tissue retractor. The wire-like filament 23 may be of various lengths, diameters, material, braided or multi-stranded fabrication, or even made from a silastic material. As well, the suture contacting surfaces of the components of the anchoring mechanism which cooperate to clamp, pinch, or retain the portion of suture line 23 may be textured or otherwise treated to tend to improve the friction between said suture line and said suture contacting surfaces.

The invention claimed is:

1. A surgical device, comprising:
 a surgical retractor having first and second oppositely disposed retractor portions operatively coupled by connecting structure and defining a space therebetween through which a surgical site is accessed;
 a suture retention device operatively coupled to said surgical retractor and adapted for retaining a surgical suture relative to said surgical retractor during a surgical intervention, said suture retention device comprising:
  a first member having a first suture contact surface; and
  a second member having a second suture contact surface, said second member being rotatable relative to said first member;
  said first member and second member configured and sized to create a retention slot therebetween for receiving a portion of the surgical suture;
 attachment structure on at least one of said first or second retractor portions and adapted to retain surgical instruments for use with said surgical retractor; and
 a suture guide channel on said surgical retractor and positioned between said retention slot and said space, whereby said suture guide channel is adapted to direct the suture from the surgical site to said retention slot between said first and second members;
 wherein said first and second suture contact surfaces cooperate to frictionally retain the surgical suture relative to said surgical retractor when said suture portion is placed within said retention slot and said second member rotates relative to said first member to bring said first and second contact surfaces into contact with the suture portion.

2. The surgical device as recited in claim 1 wherein said second member rotates by pivoting relative to said first member between a suture-retaining configuration wherein said first and second contact surfaces are in substantially proximate relationship relative to each other, and a suture-releasing configuration wherein said first and second contact surfaces are in a substantially spaced relationship relative to each other.

3. The surgical device as recited in claim 2 wherein said first and second members are configured, sized and positioned so as to frictionally retain the suture in said suture-retaining configuration by exerting a clamping force on the suture portion, said clamping force increasing when a tension is applied to the suture in at least one direction.

4. The surgical device as recited in claim 3 further comprising a support structure, wherein said first member is fixably coupled to said support structure and said second member is rotatably coupled to said support structure.

5. The surgical device as recited in claim 4 wherein said second member further comprises a pawl member, said tension applied in said at least one direction causing said pawl member to wedge the suture portion against said first contact surface and increase said clamping force in said suture-retaining configuration, said tension applied in a generally opposite direction to said at least one direction causing said clamping force to decrease and allowing the suture portion to slip relative to said first and second contact surfaces in said suture-releasing configuration.

6. The surgical device as recited in claim 2 further comprising a biasing element for biasing at least one of said first and second members towards said suture-retaining configuration.

7. The surgical device as recited in claim 2 wherein at least one of said first or second contact surfaces includes a friction-enhancing configuration for increasing friction exerted on the suture portion when said members are in said suture-retaining configuration and the suture is inserted therebetween.

8. The surgical device as recited in claim 1 wherein said second member is a lever member which is rotatably disposed adjacent said first member, said lever member having a free end including said second contact surface, the suture portion being engageable at a point of engagement between said first and second contact surfaces, said lever member being located such that a tensile action exerted on the suture induces a clamping force on the suture portion at said point of engagement.

9. The surgical device as recited in claim 1 wherein said suture retention device is removably attached to said surgical retractor.

10. The surgical device of claim 1, wherein said suture guide channel extends through said attachment structure.

11. The surgical device of claim 10, wherein:
said attachment structure comprises an attachment slot defined by a pair of opposing sidewalls and a bottom wall extending between said sidewalls, and;
said suture guide channel extends to a depth below said bottom wall of said slot to allow insertion of the suture into the suture guide channel without interfering with surgical instruments retained on said at least one first or second retractor portions.

12. A surgical device, comprising:
a surgical retractor having first and second oppositely disposed retractor portions operatively coupled by connecting structure and defining a space therebetween through which a surgical site is accessed;
at least one of said retractor portions including a suture guide channel configured to receive a segment of a surgical suture; and
a suture retention device capable of retaining the surgical suture relative to said surgical retractor during a surgical intervention, said suture retention device operatively coupled to said surgical retractor and comprising:
a first member having a first suture contact surface; and
a second member having a second suture contact surface, said second member being rotatable relative to said first member;
said first member and second member configured and sized to create a retention slot therebetween for receiving a portion of the surgical suture;
wherein said retention slot is substantially in registration and communication with said platform suture guide channel.

13. The surgical device of claim 12 wherein said surgical retractor includes an instrument-mounting rail configured for mounting a surgical instrument used during the surgical intervention and, in use, the instrument is operatively positionable with respect to said instrument-mounting rail without interference to the suture while the suture portion is received within said retention slot.

14. A surgical device, comprising:
a surgical retractor having first and second oppositely disposed retractor portions operatively coupled by connecting structure and defining a space therebetween through which a surgical site is accessed, said surgical retractor including an instrument-mounting rail configured for mounting a surgical instrument for use during the surgical intervention, said instrument-mounting rail including a suture guide channel formed therein for receiving a segment of a surgical suture; and
a suture retention device for retaining the surgical suture relative to said surgical retractor during a surgical intervention, said suture retention device operatively coupled to said surgical retractor and comprising:
a first member, said first member having a first suture contact surface; and
a second member, said second member having a second suture contact surface, said second member being rotatable relative to said first member;
said first member and said second member configured and sized to create a retention slot therebetween for receiving a portion of the surgical suture;
wherein said retention slot in said suture retention device is in communication with said suture guide channel so as to allow insertion of the suture segment into said suture guide channel and into said retention slot without interfering with the operation of said instrument-mounting rail.

15. A surgical device, comprising:
a surgical retractor including first and second oppositely disposed retractor portions operatively coupled by connecting structure and defining a space therebetween through which a surgical site is accessed;
retention device support structure on said surgical retractor;
a first member operatively coupled to said retention device support structure and having a first suture contact surface;
a second member operatively coupled to said retention device support structure and having a second suture contact surface, said second member being rotatable relative to said first member and cooperating with said first member to define a retention slot therebetween for receiving a portion of a surgical suture; and
a suture guide channel disposed between said retention slot and said space between said first and second retractor portions, whereby said suture guide channel is adapted to direct the suture from the surgical site to said retention slot between said first and second members.

16. The surgical device of claim 15, wherein said retention device support structure is disposed on one of said first and second retractor portions.

17. The surgical device of claim 15, wherein said retention device support structure is integrally formed with said surgical retractor.

18. The surgical device of claim 15, wherein said retention device support structure is selectively removable coupled with said surgical retractor.

* * * * *

UNITED STATES PATENT AND TRADEMARK OFFICE
CERTIFICATE OF CORRECTION

| | |
|---|---|
| PATENT NO. | : 8,007,515 B2 |
| APPLICATION NO. | : 11/689768 |
| DATED | : August 30, 2011 |
| INVENTOR(S) | : Anthony Paolitto et al. |

It is certified that error appears in the above-identified patent and that said Letters Patent is hereby corrected as shown below:

Column 31

Claim 12, line 46, delete "platform".

Signed and Sealed this
Tenth Day of January, 2012

David J. Kappos
*Director of the United States Patent and Trademark Office*